United States Patent
Sinko et al.

(10) Patent No.: US 9,457,099 B2
(45) Date of Patent: Oct. 4, 2016

(54) POLYETHYLENE GLYCOL-BASED DENDRONS

(75) Inventors: Patrick J. Sinko, Annandale, NJ (US); Jieming Gao, New Brunswick, NJ (US); Yashveer Singh, Highland Park, NJ (US); Xiaoping Zhang, Edison, NJ (US); Matthew S. Palombo, Marmora, NJ (US); Stanley Stein, East Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 267 days.

(21) Appl. No.: 13/296,213

(22) Filed: Nov. 14, 2011

(65) Prior Publication Data

US 2012/0183578 A1 Jul. 19, 2012

Related U.S. Application Data

(60) Provisional application No. 61/413,352, filed on Nov. 12, 2010.

(51) Int. Cl.
  *A61K 47/34* (2006.01)
  *A61K 47/48* (2006.01)
  *A61K 39/00* (2006.01)

(52) U.S. Cl.
  CPC ......... *A61K 47/48215* (2013.01); *A61K 47/34* (2013.01); *A61K 2039/6093* (2013.01); *A61K 2039/645* (2013.01)

(58) Field of Classification Search
  None
  See application file for complete search history.

(56) References Cited

U.S. PATENT DOCUMENTS

2012/0183621 A1* 7/2012 Sinko et al. .................. 424/497

OTHER PUBLICATIONS

Kozak et al., Biomacromolecules, 2009, 10, 360-365.*
Bosman, A. W. et al., About Dendrimers: Structure, Physical Properties, and Applications, Chemical Reviews 99 (7), 1665-1688, (1999)—abstract only.
Duncan, R et al.., Dendrimer biocompatability and toxity, Advanced Drug Delivery Reviews 57, 2215-2237, (2005).
Egon Buhleier, W.W., Synthesis, 155-158, (1978).
Hawker, C. J. et al., Preparation of Polymers with Controlled Molecular Architecture, A New Convergent Approach to Dendritic Macromolecules, Journal of The American Chemical Society 112, 7638-7647, (1990) (p. 1 only).
Kutscher, H. L. et al., Enhanced passive pulmonary targeting and retention of PEGylated rigid microparticles in rats, International Journal of Pharmaceutics 402, 64-71, (2010) (abstract only).
Matsumura, Y. et al., A New Concept for Macromolecular Therapeutics in Cancer Chemotherapy: Mechanism of Tumoritropic Accumulation of Proteins and the Antitumor Agent Smancs, Cancer Research 46, 6387-6392 (1986) (abstract only).
Newkome, G. R. et al., Cascade Moleculaes: A New Approach to Micelles, Journal of Organic Chemistry 50, 2003-2004 (1985) (p. 2003).
Tomalia, D. A. et al., A New Class of Polymers: Starburst-Dendritic Macromolecules, Polymer Journal 17, 117-132 (1985) (p. 117 only).

* cited by examiner

*Primary Examiner* — James H Alstrum Acevedo
*Assistant Examiner* — Roy Teller
(74) *Attorney, Agent, or Firm* — Fox Rothschild LLP

(57) ABSTRACT

The instant invention relates to polyethylene glycol-based dendrons, otherwise known as PEGtide dendrons, compositions thereof and methods of use.

16 Claims, 17 Drawing Sheets

POLYETHYLENE GLYCOL-BASED DENDRONS

CROSS-REFERENCE TO RELATED APPLICATIONS

This application claims priority under 35 U.S.C. §119(e) to U.S. Provisional Patent Application Ser. No. 61/413,352, filed on Nov. 12, 2010, the disclosure of which is incorporated herein by reference in its entirety.

GOVERNMENT SUPPORT

This invention was made with government support under AI051214 awarded by the National Institutes of Health. The federal government has certain rights in this invention.

FIELD OF THE INVENTION

The present invention relates to the synthesis of novel polyethylene glycol-based (PEGTide) dendrons, a carrier for the in vivo delivery of a therapeutic agent, compositions thereof and methods of use. In particular, this invention is directed to the PEGtide dendron composed from polyethylene glycol (PEG) and amino acids, as a carrier for the in vivo delivery of a therapeutic agent. The invention comprises a dendron structure, a tree like structure, similar in structure to a dendrimer, consisting of peptide subunits interspersed with short monodisperse poly(ethylene glycol)/PEG subunits. The PEG subunits endow dendrons with favorable pharmaceutical (e.g., long circulation time, reduced toxicity, increased water solubility etc.) and pharmacological (e.g., biocompatibility, reduced immunogenicity, biodistribution etc.) properties, generally known to be associated with PEG. PEGtide dendrons are useful for various applications including drug delivery and diagnostic purposes because they can be modified with therapeutic, targeting, biologic, and diagnostic agents.

The agent-loading mechanisms include physical encapsulation, charge interaction, covalent binding or their combinations. Payload release is performed through diffusion, carrier degradation, conjugated bond cleavage or their combinations. Compared to traditional commercial dendrimers, like polyamidoamine (PAMAM) or polypropyleneimine (PEI), PEGTide dendron owns improved biocompatibility, higher loading capability and wider application fields.

BACKGROUND OF THE INVENTION

Dendrimers (Greek: dendri: "tree-like" and meros: "part of") are monodisperse macromolecules with well-defined branched architecture and symmetrical morphology (Bosman, A. W., Chemical Reviews 99, 1665-1688, (1999)). Dendrimers are comprised of a series of branches extending outward from an inner core. These branches are arranged in layers, called generations, and represent the repeating units (monomer) of a dendrimer. A typical dendrimer molecule contains an inner core, layers of repeating units, and multiple terminal functional groups. The active moieties are either encapsulated into the core/cavities or grafted onto the surface of dendrimers. The dendrimers are distinct from other nanocarriers in that they possess a tunable structure, empty intramolecular cavity, and multifunctional surface (Duncan, R., Advanced Drug Delivery Reviews 57, 2215-2237, (2005)). The existence of interior void spaces inside the dendrimer, particularly the high generation dendrimers, becomes appropriate locations for drug or gene material loading and transportation. Generally, payloads are held inside the dendrimer Cavities via covalent attachment, hydrophobic interaction, hydrogen bonds, or charge interaction. The degradable or cleavable bonds like ester, imine, acetal and ketal are more preferred in covalent bonding since they function as the triggers of environmental response release.

The first dendrimer-like structure was reported by Vögtle and coworkers in 1978 (Egon Buhleier, W. W., Synthesis, 155-158, (1978)), who synthesized polypropylenimine (PPI). The term "dendrimer" was suggested by Tomalia et al. in 1985 who along with Newkome et al. (Newkome, G. R., Journal Of Organic Chemistry 50, 2003-2004 (1985)) synthesized dendrimers of higher generation with well-defined structures (Tomalia, D. A., Polymer Journal 17, 117-132, (1985)). The dendrimers are prepared using either divergent (Newkome, G. R., Journal Of Organic Chemistry 50, 2003-2004 (1985)) or convergent (Hawker, C. J., Journal Of The American Chemical Society 112, 7638-7647, (1990)) strategies. In a divergent approach, pioneered by Vogtle (Egon Buhleier, W. W., Synthesis, 155-158, (1978)), Donald A. Tomalia, and Newkome (Newkome, G. R., Journal Of Organic Chemistry 50, 2003-2004 (1985)), dendrimer synthesis proceeds outwards from multifunctional core to surface, whereas in a convergent approach, pioneered by Frechet and coworkers (Hawker, C. J., Journal Of the American Chemical Society 112, 7638-7647, (1990)), dendrimer synthesis proceeds inward, from surface to core. Some of the most common dendrimers are polyamidoamine (PAMAM); poly(L-lysine) (PLL); polyamide; polyester (PGLSA-OH); polypropylenimine (PEI); and poly(2,2-bis (hydroxymethyl)propionic acid (bis-MPA).

Although dendrimers have found wide application in drug and gene delivery, and diagnostics, their use is restricted due to reticuloendothelial system (RES) uptake, immunogenicity, hemolytic toxicity, cytotoxicity, hydrophobicity.

Statistics on dendrimer PEGylation shows that most of the studies have focused on dendrimer surface modification. The toxicity from dendrimer branch/core structure is still a potential threat for safe use of dendrimers. In addition, since the sizes of currently developed dendrimers are less than 100 nanometers, these are prone to excretion by kidney.

SUMMARY OF THE INVENTION

The present invention relates to the synthesis of novel polyethylene glycol-based (PEGTide) dendrons, a carrier for the in vivo delivery of a therapeutic agent, and its application in drug delivery, diagnostic applications, vaccines and related methods to treat a condition, and generate an immune response.

Developing novel dendrons with larger size (100 to 200 nm) is needed in order to meet the advanced requirements of drug delivery applications in the pharmaceutical field, including better biocompatibility, higher size, and tunable interior void size/structure, design. The development of a PEGtide dendron is disclosed in this patent.

An embodiment of the present invention is a carrier for the in vivo delivery of a therapeutic agent represented by Formula 1:

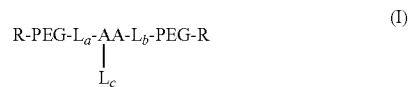

(I)

wherein R is:

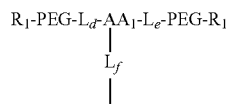

$R_1$ is:

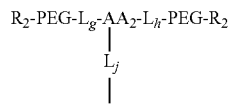

$R_1$ is:

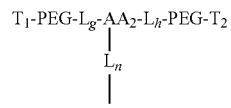

PEG is linear or branched poly(ethylene glycol);

AA, $AA_1$, $AA_2$, and $AA_3$ are each independently lysine or ornithine;

$L_a$, $L_b$, $L_c$, $L_d$, $L_e$, $L_f$, $L_g$, $L_h$, $L_j$, $L_k$, $L_m$, and $L_n$ are each independently 0-8 amino acids long and selected from alanine, glycine, val-ine, leucine, isoleucine, statine, phenylglycine, phenylalanine, cysteine, penicillamine, homocysteine, arginine, histidine, norvaline, norleucine, 2-fluorophenylalanine, 3-fluorophenylalanine, 4-fluorophenylalanine, β-cyclohexyl-alanine, 2-aminobutyric acid, 4-aminobutyric acid, 6-aminobutyric acid and α-aminobutyric acid; and $T_1$ and $T_2$ are each a final PEG terminus independently selected from an amino group, acetyl group, fluorenylmethyloxycarbonyl group, therapeutic agent, diagnostic agent, biologic agent, targeting agents, or adjuvant.

In certain embodiments, $L_c$ may be selected from cysteine, penicillamine, homocysteine and alanine.

In certain embodiments, Formula (I) may not contain $L_a$, $L_b$, $L_c$, $L_d$, $L_e$, $L_f$, $L_g$, $L_h$, $L_j$, $L_k$, $L_m$, or $L_n$. In certain other embodiments, Formula (I) may be represented by:

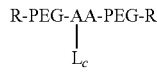

In certain embodiments, Formula (I) may not contain PEG. In certain other embodiments, R may not contain PEG, and Formula (I) may be represented wherein R is:

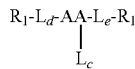

In certain embodiments, R may not contain $L_d$ or $L_e$. In certain embodiments, $R_1$ may not contain PEG. In certain embodiments, $R_1$ may not contain $L_g$ or $L_h$. In certain embodiments, $R_2$ may not contain PEG. In certain embodiments, $R_2$ may not contain $L_k$ or $L_m$.

In certain embodiments, the $T_1$ and $T_2$ amino groups are selected from free amino groups, protected amino groups and amino groups modified with therapeutic agent.

In certain embodiments, $R_2$ is $T_1$ or $T_2$.

In certain embodiments, AA, $AA_1$, $AA_2$, and $AA_3$ are each lysine; $L_a$, $L_b$, $L_c$, $L_d$, $L_e$, $L_f$, $L_g$, $L_h$, $L_j$, $L_k$, $L_m$, and $L_n$ are selected from alanine, arginine or histidine; $T_1$ and $T_2$ are fluorenylmethyloxycarbonyl protected amino groups.

In certain embodiments, AA, $AA_1$, $AA_2$, and $AA_3$ are each lysine; $L_a$, $L_b$, $L_c$, $L_d$, $L_e$, $L_f$, $L_g$, $L_h$, $L_j$, $L_k$, $L_m$, and $L_n$ are each alanine; $T_1$ and $T_2$ are fluorenylmethyloxycarbonyl protected amino groups.

In accordance with any of the above embodiments, the invention further comprises at least one therapeutic agent. In a further embodiment, a therapeutic agent may be a pharmaceutically active, diagnostic, biologic, imaging, targeting agent or an adjuvant.

In accordance with any of the above embodiments, the invention may further comprise at least one therapeutic agent and a pharmaceutically acceptable carrier. In a further embodiment, a therapeutic agent may be an antineoplastic or an antiretroviral agent.

In accordance with any of the above embodiments, the invention may be a vaccine comprising a composition represented by Formula 1.

The present invention further provides a method for treating a condition linked to a hyperproliferative disorder, comprising administering to a patient in need thereof an effective amount of a composition represented by Formula 1 further comprising an antineoplastic agent.

The present invention also provides a method for treating stimulating an immune response, comprising administering to a patient in need thereof an effective amount of a vaccine comprising a composition represented by Formula 1 further comprising an antigen.

BRIEF DESCRIPTION OF THE DRAWINGS

FIG. 9 is a schematic of the synthesis of PEGTide dendrons.

DETAILED DESCRIPTION OF THE INVENTION

1. Overview

Figure 1:
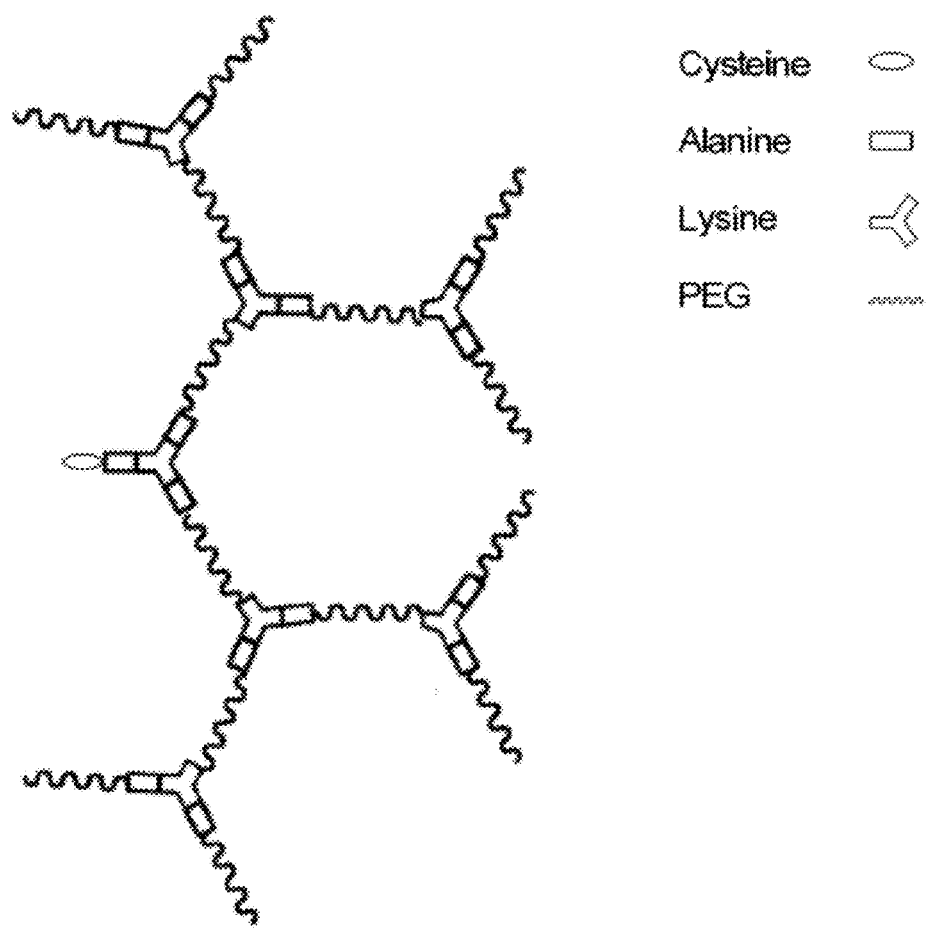
FIG. 1 depicts the structure of a generation 3.0 (G3.0) PEGtide dendron.

The instant invention relates to polyethylene glycol-based dendrons, otherwise known as PEGtide dendrons, a carrier for the in vivo delivery of a therapeutic agent, compositions thereof and methods of use. PEGTide dendrons are synthesized with tunable nanostructure by regulating size, shape, surface chemistry, and interior void space. Current applications for commercial dendrons, or their surface-modified products, include drug/gene delivery and/or imaging. With the increase of generation in dendrimers like PAMAM or PEI dendrimers, positive charges increase and therefore the toxicity of the carrier also increases. This is not the case with PEGtide dendrons because the dendritic tree like structure is interspersed with biocompatible PEG subunits. In order to improve the biocompatibility and enlarge the application area, novel polyethylene glycol-based dendrons (PEGTide) are designed and synthesized.

2. Definitions

As used above, and throughout the description of the invention, the following terms, unless otherwise indicated, shall be understood to have the following meanings:

As used herein, the singular forms "a," "an" and "the" include plural references unless the content clearly dictates otherwise.

The term "about", as used here, refers to +/−10% of a value.

As used herein, the term "linker" refers to a chemical moiety that connects a molecule to another molecule, covalently links separate parts of a molecule or separate molecules. The linker provides spacing between the two molecules or moieties such that they are able to function in their intended manner. Examples of linking groups include peptide linkers, enzyme sensitive peptide linkers/linkers, self-immolative linkers, acid sensitive linkers, multifunctional organic linking agents, bifunctional inorganic crosslinking agents and other linkers known in the art. The linker may be stable or degradable/cleavable.

As used herein the term "therapeutic agent" encompasses pharmaceutically active therapeutic agents, diagnostic, biologic and targeting agents, as well as adjuvants.

As used herein, the term "diagnostic agent" refers to any molecule which produces, or can be induced to produce, a detectable signal. The diagnostic agent may be any diagnostically useful compound that may be bound via a functional group thereon to the composition of the invention. Diagnostic moieties having reporter molecules that can be detected by imaging equipment may include radioactive, paramagnetic, fluorescent or radioopaque chemical entities. Non-limiting examples of labels include radioactive isotopes, enzymes, enzyme fragments, enzyme substrates, enzyme inhibitors, coenzymes, catalysts, fluorophores, dyes, chemiluminescers, luminescers or sensitizers; a non-magnetic or magnetic particle, iodinated sugars used as radioopaque agents, and can be appended to linker backbones using ester or other linkages.

As used herein, the term "biologic agent" encompasses substances generally derived from a biological source, such as from an organism, a cell line, an isolated tissue, or the like which includes proteins, peptides, carbohydrates, polysaccharides, nucleic acid molecules, examples include antibodies and fragments thereof (including humanized, single chain, chimeric antibodies, fab regions, fc regions, complementarity determining regions, and any combination thereof), peptides (including hormones, for example insulin), nucleic acid molecules (including DNA, RNAs, microRNAs, siRNAs, shRNAs, and tRNAs, antisense, aptamers, ribozymes, external guide sequences for ribonuclease P, and triplex forming agents), and antigens, antigenic agents, immunogens and haptens.

As used herein the term "nucleic acid" refers to a molecular entity composed of a nucleobase, sugar moiety, and phosphate group, or analogs thereof, including DNA, RNAs, microRNAs, siRNAs, shRNAs, and tRNAs. Examples include the DNA nucleotides, i.e., adenine, guanine, cytosine, and thymidine, or the RNA nucleotide uracil, or synthetic analogs thereof. Examples of sugar moieties to which the nucleobases are covalently bonded include but are not limited to ribose and deoxyribose. Analogs of sugars can also be present; for example, halodeoxyribose analogs.

As used herein the term "peptide" is used interchangeably with the term "protein" and "amino acid sequence", in its broadest sense refers to a compound of two or more subunit amino acids, amino acid analogs or peptidomimetics.

As used herein, the term "amino acid" refers to natural and/or unnatural or synthetic amino acids, including glycine and both the D and L optical isomers, amino acid analogs (for example norleucine is an analog of leucine) and peptidomimetics.

As used herein, "targeting agents" refer to ligands, polymers, proteins, cytokines, chemokines, peptides, nucleic acids, lipids, saccharides or polysaccharides, small molecules or any combination thereof, (for example a glycolipid, glycoprotein etc) that bind to a receptor or other molecule on the surface of a targeted cell. An exemplary small-molecule targeting compound is folate, which targets the folate receptor. The degree of specificity can be modulated through the selection of the targeting molecule. For example, antibodies are very specific. These can be polyclonal, monoclonal, fragments, recombinant, or single chain, many of which are commercially available or readily obtained using standard techniques. Examples of antibodies include, but not limited to abciximab, basiliximab, cetuximab, infliximab, rituximab, trastuzumab etc.

Additional examples of targeting agents include RGD peptide, EGF peptide, DV3 (LGASWHRPDKC) peptide, a LYP peptide (CGNKRTRGC), a membrane-binding domain of IGFBP3 (QCRPSKGRKRGFCW), fMLF, luteinizing hormone releasing hormone (LHRH), mannose, transferrin ligand and monoclonal antibodies, including the drug conjugated derivatives of the above mentioned agents.

As used herein, the term "dendron" encompasses polymers distinguished by their repeated branching structure emanating from a central core. The term dendron also encompasses dendrimers. Preferably the polymer is monodisperse PEG. Biocompatible PEG may be present throughout the dendritic structure, and is not restricted to the core or surface:

As used herein, the terms "polymer," "polymeric" and similar terms have the usual meaning known to those skilled in the art and thus may be used to refer to homopolymers, copolymers (e.g., random copolymer, alternating copolymer, block copolymer, graft copolymer) and mixtures thereof.

As used herein, "PEG", is used herein as an abbreviation for polyethylene glycol. PEGs are included within the broader class of polyalkylene oxides, which include PEG as well as polypropylene glycols, and polyglycol copolymers. PEG can have a range of molecular weights. The PEG molecular weight range contemplated for use in the present invention is from about 100 to about 1000 Da.

"Animal" includes all vertebrate animals including humans. In particular, the term "vertebrate animal" includes, but not limited to, mammals, humans, canines (e.g., dogs), felines (e.g., cats); equines (e.g., horses), bovines (e.g., cattle), porcine (e.g., pigs), mice, rabbits, goats, as well as in avians. The term "avian" refers to any species or subspecies of the taxonomic class ava, such as, but not limited to, chickens (breeders, broilers and layers), turkeys, ducks, geese, quail, pheasants, parrots, finches, hawks, crows and ratites including ostrich, emu and cassowary.

The term "pharmaceutical composition" refers to the combination of an active therapeutic agent with a carrier, inert or active, making the composition especially suitable for diagnostic or therapeutic use in vivo or ex vivo.

A "pharmaceutically acceptable carrier," after administered to or upon a subject, does not cause undesirable physiological effects.

The term "immunogenic" refers to a capability of producing an immune response in a host animal against an antigen or antigens.

"Immune response" refers to a response elicited in an animal, which may refer to cellular immunity, humoral immunity or both. This immune response forms the basis of the protective immunity elicited by a vaccine against a specific infectious organism.

"Antigenic agent," "antigen," or "immunogen" means a substance that induces a specific immune response in a host animal. It can be a molecule containing one or more epitopes (either linear, conformational or both) that elicit an immunological response. The term "epitope" refers to basic element or smallest unit of recognition by an individual antibody, B-cell receptor, or T-cell receptor, and thus the particular domain, region or molecular structure to which said antibody or T-cell receptor binds. An antigen may consist of numerous epitopes while a hapten, typically, may possess few epitopes.

As used herein, the term "hapten" refers to a low-molecular weight organic compound that is not capable of eliciting an immune response by itself but will elicit an immune response once attached to a carrier molecule.

3. Pegtide Dendrons

The present invention provides a carrier for the in vivo delivery of a therapeutic agent according to Formula 1:

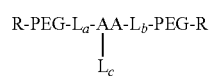

wherein R is:

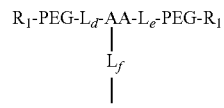

$R_1$ is:

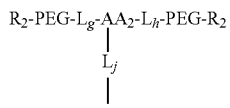

$R_2$ is:

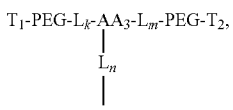

PEG is linear or branched poly(ethylene glycol);

$AA, AA_1, AA_2,$ and $AA_3$ are each independently lysine or ornithine;

$L_a, L_b, L_c, L_d, L_e, L_f, L_g, L_h, L_j, L_k, L_m$ and $L_n$ are each independently 0-8 amino acids long and selected from alanine, glycine, val-ine, leucine, isoleucine, statine, phenylglycine, phenylalanine, cysteine, penicillamine, homocysteine, arginine, histidine, norvaline, norleucine, 2-fluorophenylalanine, 3-fluorophenylalanine, 4-fluorophenylalanine, β-cyclohexyl-alanine, 2-aminobutyric acid, 4-aminobutyric acid, 6-aminobutyric acid and α-amino-butyric acid;

$T_1$ and $T_2$ are each a final PEG terminus independently selected from an amino group, acetyl group, fluorenylmethyloxycarbonyl group, therapeutic agent, diagnostic agent, biologic agent, targeting agents, or adjuvant. Amino groups are selected from free amino groups, protected amino groups and amino groups modified with therapeutic agent.

In certain embodiments, $L_c$ may be selected from cysteine, penicillamine, homocysteine and alanine.

In certain embodiments, Formula (I) may not contain $L_a, L_b, L_c, L_d, L_e, L_f, L_g, L_h, L_j, L_k, L_m$ or $L_n$. In certain other embodiments, Formula (I) may be represented by:

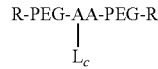

In certain embodiments, Formula (I) may not contain PEG. In certain other embodiments, R may not contain PEG, and Formula (I) may be represented wherein R is:

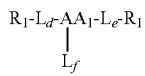

In certain embodiments, R may not contain $L_d$ or $L_e$. In certain embodiments, $R_1$ may not contain PEG. In certain embodiments, $R_1$ may not contain $L_g$ or $L_h$. In certain embodiments, $R_2$ may not contain PEG. In certain embodiments, $R_2$ may not contain $L_k$ or $L_m$.

One embodiment of the present invention includes a "third generation" (G3.0) dendron wherein $R_2$ is selected from the group consisting of $T_1$ and $T_2$.

Another embodiment includes a "fourth generation" (G4.0) dendron in which $R_2$ is:

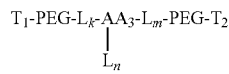

In certain embodiments, AA, $AA_1$, $AA_2$, and $AA_3$ are each lysine; $L_a$, $L_b$, $L_c$, $L_d$, $L_e$, $L_f$, $L_g$, $L_h$, $L_j$, $L_k$, $L_m$, and $L_n$ are selected from alanine, arginine or histidine; $T_1$ and $T_2$ are fluorenylmethyloxycarbonyl protected amino groups.

In certain embodiments, AA, $AA_1$, $AA_2$, and $AA_3$ are each lysine; $L_a$, $L_b$, $L_c$, $L_d$, $L_e$, $L_f$, $L_g$, $L_h$, $L_j$, $L_k$, $L_m$ and $L_n$ are each alanine; $T_1$ and $T_2$ are fluorenylmethyloxycarbonyl protected amino groups.

$T_1$ and $T_2$ are each a final PEG terminus selected from an amino group, acetyl group, fluorenylmethyloxycarbonyl group; therapeutic, diagnostic, biologic and targeting agents, as well as adjuvants, or any combination thereof.

In another embodiment, $T_1$ and $T_2$ are free or protected amino groups or amino groups modified with therapeutic agents. Examples of commonly used amine-protecting groups include, but are not limited to, carboxybenzyloxy (CbZ), tert-butyloxycarbonyl (Boc), 9-fluorenyl-methyloxycarbonyl (Fmoc), acetyl (Ac), benzyl (Bz), triphenylmethyl (Trityl), 2,2,4,6,7-pentamethyldihydrobenzofuran-5-sulfonyl (pbf), 1-(4,4,-dimethyl-2,6-dioxo-cyclohexylodene)-3-methyl butyl (ivDe), 4-methyltrityl (MTT), 4-methoxytrityl (MMT), t-butyl (tBu), adamantyloxy (AdaO), and the like.

In one embodiment, the polyethylene glycol has a molecular weight between about 100 and about 1000 Da. In another embodiment, the polyethylene glycol has a molecular weight between about 250 and about 750 Da, In yet another embodiment, the polyethylene glycol has a molecular weight between about 400 and about 600 Da.

Dendrons can be further joined together directly or through a multifunctional core (convergent approach).

Dendrons may contain monodisperse PEG alternating with dipeptide K-β-A, which leads to the formation of a monodisperse dendritic structure with no structural heterogeneity.

Figure 18:
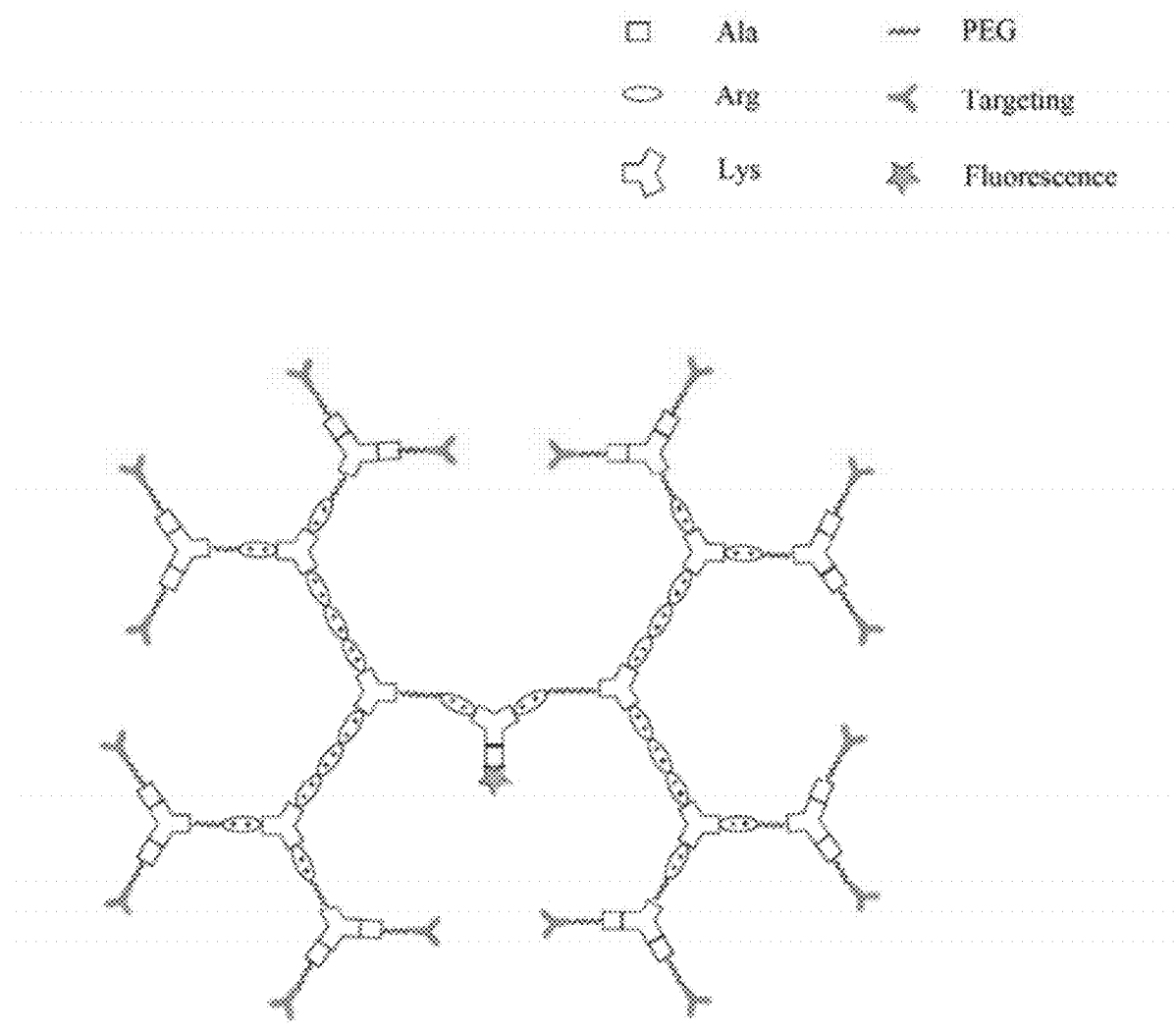
FIG. 18 depicts the structure of PEGtide dendron G4.0 for siRNA/DNA delivery, the structure contains peripheral functional moieties for cell targeting delivery; arginine for nucleic acid binding.

It is possible to develop dendrons with different structure, including sizes and densities, and multiple functionalities by altering the monodisperse PEG and amino acids incorporated in dendrons. For example, it is possible to incorporate amino acids like arginine and histidine to complex the dendron with antisense oligonucleotides/siRNA as illustrated in FIG. 18.

One of ordinary skill in the art will appreciate the various embodiments that may be synthesized, and used in the presently described and claimed invention.

4. Pharmaceutical Compositions

The present invention provides a pharmaceutical invention comprising the PEGtide dendrons of the present invention and a therapeutic agent, and may include a pharmaceutically acceptable carrier, suitable for administration to a mammal, fish, bird, preferably a human. To administer the pharmaceutical composition to humans or animals, it is preferable to formulate the molecules in a composition comprising one or more pharmaceutically acceptable carriers. The phrase "pharmaceutically acceptable" refers to molecular entities and compositions that do not produce allergic, or other adverse reactions when administered using routes well-known in the art. "Pharmaceutically acceptable carriers" include any and all clinically useful solvents, dispersion media, coatings, antibacterial and antifungal agents, isotonic and absorption delaying agents and the like.

The loading of therapeutic agents is achieved by any or the combination of following mechanisms: (i) physical encapsulation; (ii) complexation/charge interactions; and (iii) covalent conjugation via non-degradable or degradable bonds. Physical encapsulation is achieved by mixing the therapeutics with the dendron in varying proportions in solvent or solvent systems. Charged interactions involve the creation of multiple charged centers with in the dendron or the dendron surfaces for complexation with therapeutic agents containing opposite charges. For example, multiple arginine moieties are incorporated in the dendron to make it cationic, which then complexes the anionic biomolecules (oligonucleotides like antisense, siRNA etc.) into nano-sized materials. The therapeutic agents are also attached to PEGtide dendrons via non-degradable and/or degradable covalent bonds. Covalent attachment is achieved by incorporating mutually reactive functional groups on the therapeutic agent and the dendron or by using homo- and/or hetero-multifunctional cross linkers. The examples of degradable covalent bonds include, but not limited to, enzyme-sensitive peptide linkers and bonds; auto-degradable ester and thioester bonds; acid-sensitive bonds like imines, hydrazones, carboxylic hydrazones, ketal, acetal, cis-aconityl, and trityl bonds; hypoxia-sensitive linkers; and self-immolative bonds. BIOCONJUGATE TECHNIQUES (Academic Press; 1st edition, Greg T. Hermanson, 1996) describes techniques for modifying or crosslinking of biomolecules.

The therapeutic agent is released from the dendron by following mechanisms: (i) passive diffusion; (ii) degradation of protease-sensitive amide bonds used in the dendron construct; and (iii) degradation of covalent bond linking the therapeutic agent to the dendron.

PEGtide dendrons are also used for targeted delivery. Targeting or targeted drug delivery involves delivering therapeutic agents to specific organs, tissue, cells, intracellular organelles or molecules. Targeting is achieved by any or combination of following mechanisms: (i) passive targeting (mononuclear phagocyte system, enhanced permeability and retention effect); and (ii) active targeting.

Particulate systems are taken up by mononuclear phagocyte system (MPS) leading to eventual loss of therapeutic agents. Grafting of PEGs on the dendron surfaces diminishes the uptake of nanoparticulate systems by MPS. The same route is used for developing macrophage-targeted therapies. PEGtide dendrons are also used for passive targeting to tumors by the enhanced permeability and retention (EPR) effect. Unlike the normal tissue, the blood vessels in tumor tissues are leaky and therefore extensive leakage of blood plasma content (macromolecules, nanoparticles, lipidic particles) occurs into the tumor, due to its enhanced permeability. Since the lymphatic drainage in tumor tissue is also impaired, the leaked contents exhibit size-dependent retention in tumor tissues. Another reason size is critical in many delivery applications is because molecules with smaller size (<5 nm) are rapidly eliminated by kidneys. The PEG molecules display large hydrodynamic radii (larger than expected from its molecular weight) because 2-3 molecules of water surround each ethylene glycol moiety in PEG. The PEGtide dendrons, in range of 100-200 nm, could be suitable candidate for passive targeting to tumors by enhanced permeability and retention (EPR) effect (Matsumura, Y., *Cancer Research* 46, 6387-6392, (1986)). The passive tumor targeting properties of PEGtide dendrons are controlled by varying the molecular size of the PEG incorporated in the dendron.

Active targeting is achieved by covalently attaching antibodies or ligands on the dendron, which selectively recognizes the antigens or surface receptors expressed on the target cells. The examples of antibodies include, but not limited to abciximab, basiliximab, cetuximab, infliximab, rituximab, trastuzumab etc. Similarly, the targeting ligands include, but not limited to, peptides, hormones, vitamins, growth factors, carbohydrates. Examples include, but not limited to, folic acid, cyclic or linear peptides with RGD motif, peptides with EGF motif, DV3 peptide, Lyp peptide, peptide binding domain of IGFBP3, fMLF, luteinizing hormone releasing hormone (LHRH), transferrin, β-galactoside or β-N-acetylgalactosamine, mannose etc. The PEGtide dendrons have multiple attachment sites (functional groups) on the surface, which is used to anchor/graft multiple targeting antigens/ligands for multivalent targeting.

The present invention provides for a pharmaceutical composition comprising of multiple therapeutic agents, as well as various types of therapeutic agents. For example, a pharmaceutical agent may comprise a diagnostic agent and a pharmaceutically active agent bound to a PEGtide dendreon. In another example, multiple types of agents may be bound to a PEGtide dendreon, such as at least one pharmaceutically active agent, at least one biologic agent, at least one diagnostic agent and at least one targeting agent, or various combinations thereof.

Examples of pharmaceutically acceptable carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

Antineoplastic agents are used to treat cancer, and examples of antineoplastic agents include, but not limited to, Abarelix, Aldesleukin, Alemtuzumab, Alitretinoin, Allopurinol, Altretamine, Amifostine, Anastrozole, arsenic trioxide, asparaginase, azacitidine, bevacuzimab, bleomycin, bortezomib, capecitabine, carboplatin, carmustine, celecoxib, cetuximab, chlorambucil, cisplatin, cladribine, clofarabine, cyclophosphamide, cytarabine, dacarbazine, daunorubicin, daunomycin, dexrazoxane, docetaxel, doxonibicin, epirubicin, Epoetin alfa, Erlotinib, Estramustine, etoposide phosphate, etoposide, VP-16, exemestane, Filgrastim, Floxuridine, Fludarabine, fluorouracil, 5-FU, fulvestrant, gefitinib, gemcitabine, gemtuzumab, goserelin acetate, histrelin acetate, hydroxyurea, idarubicin, ifosfamide, imatinib mesylate, interferon alfa 2a, irinotecan, lenalidomide, letrozole, leucovorin, Leuprolide Acetate, Levamisole, lomustine, CCNU, mechlorethamine, nitrogen mustard, megestrol acetate, melphalan, L-PAM, mercaptopurine, 6-MP, mesna, methotrexate, methoxsalen, mitomycin C, mitotane, mitoxantrone, nelarabine, Nofetumomab, Oprelvekin, Oxaliplatin, Paclitaxel, Palifermin, Pamidronate, Pegademase, pemetrexed disodium, pentostatin, pipobroman, plicamycin, mithramycin, porfimer sodium, procarbazine, quinacrine, Rasburicase, Rituximab, Sargramostim, Sorafenib, Streptozocin, sunitinib maleate, tamoxifen, temozolomide, teniposide, VM-26, testolactone, thioguanine, 6-TG, thiotepa, topotecan, toremifene, Tositumomab, Trastuzumab, Uracil Mustard, Valrubicin, Vinblastine, Vincristine, Vinorelbine, Zoledronate, and zoledronic acid.

Antiretroviral agents are drug used to treat infection by retroviruses, and examples antiretroviral agents include, but not limited to nucleoside reverse transcriptase inhibitors (NRTIs), such as efavirenz, tenofovir, emtricitabine, zidovudine, lamivudine, abacavir, didanosine, stavudine; Non-nucleoside reverse transcriptase inhibitors (NNRTIs), such as efavirenz, delavirdine, nevirapine, etravirine, lersivirine, rilpivirine; protease inhibitors (PIs), such as: saquinavir, ritonavir, indinavir, nelfinavir, amprenavir, lopinavir, atazanavir, fosamprenavir, tipranavir, darunavir; Fusion inhibitors, such as: maraviroc, enfuvirtide, TNX-355, PRO140, BMS-488043, plerixafor, epigallocatechin gallate, vicriviroc, aplaviroc, griffithsin, DCM205; HIV integrase strand transfer inhibitors, such as raltegravir.

Anti-inflammatory agents are used to reduce inflammation, and examples of anti-inflammatory agents include, but not limit to, diclofenac, esomeprazole, etodolac, fenoprofen, flurbiprofen, aspirin, ibuprofen, indomethacin, ketoprofen, ketorolac, lansoprazole, meclofenamate, mefenamic acid, meloxicam, nabumetone, naproxen, oxaprozin, piroxicam, sulindac, tolmetin, paracetamol, dexamethasone, glucocorticoid.

Antimicrobial agents are used to kill or inhibit the growth of microorganism, and examples of anti-microbial agents include, but not limit to, Sulfonamides, isoniazid, p-aminosalicylic acid, penicillin, streptomycin, tetracyclines, chloramphenicol, erythromycin, novobiocin, neomycin, bacitracin, polymyxin, emetine, quinine, griseofulvin, nystatin, neomycin.

Antiretroviral agents are drugs used to treat infection by retroviruses, and examples antiretroviral agents include, but not limited to nucleoside reverse transcriptase inhibitors (NRTIs), such as efavirenz, tenofovir, emtricitabine, zidovudine, lamivudine, abacavir, didanosine, stavudine; Non-nucleoside reverse transcriptase inhibitors (NNRTIs), such as efavirenz, delavirdine, nevirapine, etravirine, lersivirine, rilpivirine; protease inhibitors (PIs), such as: saquinavir, ritonavir, indinavir, nelfinavir, amprenavir, lopinavir, atazanavir, fosamprenavir, tipranavir, darunavir; Fusion inhibitors, such as: maraviroc, enfuvirtide, TNX-355, PRO140, BMS-488043, plerixafor, epigallocatechin gallate, vicriviroc, aplaviroc, griffithsin, DCM205; HIV integrase strand transfer inhibitors, such as raltegravir.

The invention also relates to a pharmaceutical composition for the treatment of a hyperproliferative disorder or inflammatory disease or an autoimmune disease in a mammal which comprises a therapeutically effective amount of a compound of the invention and a pharmaceutically acceptable carrier. In one embodiment said pharmaceutical composition is for the treatment of cancer, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma, and other cancers yet to be determined in which CD38 is expressed predominantly. In a preferred embodiment, the pharmaceutical compositions of the invention are used for the treatment of a cancer such as non-Hodgkin's lymphoma, Hodgkin's lymphoma, hairy cell leukemia, multiple myeloma, chronic lymphocytic leukemia, chronic myeloid leukemia, acute myeloid leukemia, or acute lymphocytic leukemia, in which CD38 is expressed, and other cancers yet to be determined in which CD38 is expressed predominantly. In another embodiment, the pharmaceutical composition of the invention can be used to treat autoimmune diseases, such as systemic lupus erythematosus, rheumatoid arthritis, multiple sclerosis, Crohn's disease, ulcerative colitis, gastritis, Hashimoto's thyroiditis, ankylosing spondylitis, hepatitis C-associated cryoglobulinemic vasculitis, chronic focal encephalitis, bulbous pemphigoid, hemophilia A, membranoproliferative glomerulnephritis, Sjogren's syndrome, adult and juvenile dermatomyositis, adult polymyositis, chronic urticaria, primary biliary cirrhosis, idiopathic thrombocytopenic purpura, neuromyelitis optica, Graves' dysthyroid disease, bullous pemphigoid, membranoproliferative glonerulonephritis, Churg-Strauss syndrome, and asthma. In another embodiment, said pharmaceutical composition relates to other disorders such as, for example, graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

When the pharmaceutical composition of the present invention is used as a medicament, the compound of the present invention is mixed with a pharmaceutically acceptable carrier (excipient, binder, disintegrant, corrigent, flavor, emulsifier, diluent, solubilizing agents and the like) to give a pharmaceutical composition which can be orally or parenterally administered. A pharmaceutical composition can be formulated by a general method.

In the present specification, parenteral includes subcutaneous injection; intravenous injection, intramuscular injection, intraperitoneal injection, drip or topical administration (transdermal administration, transocular administration, transpulmonary or bronchial administration, transnasal administration, transrectal administration and the like) and the like.

The dose of the pharmaceutical composition of the present invention is determined according to the age, body weight, general health condition, sex, diet, administration time, administration method, clearance rate, and the level of disease for which patients are undergoing treatments at that time, or further in consideration of other factors. While the daily dose of the compound of the present invention varies depending on the condition and body weight of patient, the kind of the compound, administration route and the like, it is parenterally administered at, for example, 0.01 to 100 mg/patient/day by subcutaneous, intravenous, intramuscular, transdermal, transocular, transpulmonary or bronchial, transnasal or rectal administration.

Oral dosage forms may include capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In particular examples, an oral dosage range is from about 1.0 to about 100 mg/kg body weight administered orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated.

5. Vaccine

The composition comprising according to Formula I described above can be used in a vaccine formulation to immunize an animal. Thus, this invention also provides an immunogenic or antigenic composition (a vaccine) that contains a pharmaceutically acceptable carrier and an effective amount of a composition comprising Formula I described above further comprising an antigen, immunogen, epitope or a hapten. The pharmaceutically acceptable carriers used in the vaccine can be selected on the basis of the mode and route of administration, and standard pharmaceutical practice.

Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

A vaccine formulation may be administered to a subject per se or in the form of a pharmaceutical composition as previously described. A vaccine containing a biologic agent (such as a hapten, antigen, immunogen, eptope) and an adjuvant may be manufactured by means of conventional mixing, dissolving, granulating, dragee-making, levigating, emulsifying, encapsulating, entrapping or lyophilizing processes. A vaccine may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

Examples of an adjuvant include a cholera toxin, *Escherichia coli* heat-labile enterotoxin, liposome, unmethylated DNA (CpG) or any other innate immune-stimulating complex. Various adjuvants that can be used to further increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum.*

An effective amount refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment.

The amount of a composition administered depends, for example, on the particular antigen in the vaccine, whether an adjuvant is co-administered with the antigen, the type of adjuvant co-administered, the mode and frequency of administration, and the desired effect (e.g., protection or treatment), as can be determined by one skilled in the art. Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, the vaccine formulations of the invention may be administered in about 1 to 3 doses for a 1-36 week period. Preferably, 1 or 2 doses are administered, at intervals of about 3 weeks to about 4 months; and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the patient, but will typically range from about 0.1 mL to about 5 mL. Sera can be taken from the subject for testing the immune response or antibody production elicited by the composition against the antigen. Methods of assaying antibodies against a specific antigen are well known in the art. Additional boosters can be given as needed. By varying the amount of the composition and frequency of administration, the protocol can be optimized for eliciting a maximal production of the antibodies.

A vaccine of this invention can be administered parenterally, orally, nasally, rectally, topically, or buccally. The term "parenteral" includes subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils can be conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A vaccine for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In certain embodiments the antigen can come from a disease-causing microorganism or a parasite. For example, the antigen can be one from a virus, e.g., a flu invariant helix to elicit flu immunity, especially pan-flu immunity. Other influenza antigens can be used to elicit immunity to various distinct influenza types or other antigen of viral origin.

Examples of suitable antigens, epitopes, or immunogenic moieties include viral, bacterial, or parasitic antigens; inactivated viral, tumor-derived, protozoal, organism-derived, fungal, or bacterial antigens; toxoids, toxins; self-antigens; polysaccharides; lipids, fatty acids, proteins; glycoproteins; peptides; cellular vaccines; DNA vaccines; recombinant proteins; glycoproteins; and the like, for use in eliciting immune response to, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus and yellow fever, and Alzheimer's Disease. Especially, materials (such as recombinant proteins, glycoproteins, peptides, and haptens) that otherwise do not raise a strong immune response can be used in connection with the invention so as to elicit satisfactory response.

In some embodiments, the epitope can be a portion of a cancer antigen, such that antibodies against the epitope can raise specific anti-cancer immunity. This will be particularly interesting in situations where passive infusion of specific antibodies is known to be therapeutic (as is the case with neurofibromatosis, a childhood cancer), or where specific anti-tumor antibodies can bind to receptors present in certain cancer tissues (e.g. breast) and inhibit cancer growth (e.g. Trastuzumab/herceptin, broadly used in breast cancer treatment to block neu/her receptors).

In a further embodiment, the vaccine can target the mannose receptor of macrophages, by conjugating mannose to the dendron in conjunction with a cancer antigen to stimulate the immune system conferring specific anti-cancer immunity.

The terms cancer antigen and tumor antigen are used interchangeably and refer to an antigen that is differentially expressed by cancer cells. Cancer antigens can be exploited to differentially target an immune response against cancer cells, and stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-C017-1A/GA733, Carcinoembryonic Antigen (CEA) and its antigenic epitopes CAP-1 and CAP-2, etv6, am11, Prostate Specific Antigen (PSA) and its antigenic epitopes PSA-1, PSA-2, and PSA-3, prostate-specific membrane antigen (PSMA), T-cell receptor/CD3-.zeta. chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, am11, cyclophilin b), B cell lymphoma (Ig-idiotype), glioma (E-cadherin, α-catenin, β-catenin, gamma-catenin, and p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUG family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100), myeloma (MUC family, p21 ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

EXAMPLES

The following non-limiting examples set forth herein below illustrate certain aspects of the invention.

Example 1

Materials and Methods

Fmoc-N-amido-dPEG®$_6$-acid (MW 575.65 Da, Fmoc-PEG$_6$-OH) was purchased from Quanta Biodesign Ltd. (Powell, Ohio); Fmoc-β-Ala-Wang Resin, Fmoc-Lys (Fmoc)-OH, Fmoc-β-Ala-OH, benzotriazole-1-yl-oxy-tris-pyrrolidino-phosphonium hexafluorophosphate (PyBOP) were purchased from EMD Chemicals (Gibbstown, N.J.); Fmoc-Lys (5-FAM)-OH and 4",6-diamidino-2-phenylindole, dihydrochloride (DAPI) were purchased from Anaspec (Fremont, Calif.); 1-hydroxybenzotrizole (HOBT) was purchased from Chem-Impex International (Wood Dale, Ill.); piperidine, α-D-mannopyranosylphenyl isothiocyanate, triisopropylsilane and sinapinic acid were purchased from Sigma-Aldrich (St. Louis, Mo.); N,N-dimethylformamide (DMF), acetic anhydride, N,N-diisopropylethylamine (DIPEA) were purchased from Acros Organics (Morris Plains, N.J.); trifluoroacetic acid (TFA) was purchased from Fisher Scientific (Pittsburgh, Pa.); diethyl ether was purchased from Honeywell Brudick & Jackson (Muskegon, Mich.); and PD-10 column was purchased from GE Healthcare (Piscataway, N.J.). The J774.E murine macrophage cell was a donation from Dr. Philip D. Stahl, Washington University (St. Louis, Wash.). Chambered Coverglass (Lab-Tek™ II) was obtained from Thermo Scientific (Rochester, N.Y.). Hanks' balanced salt solution (HBSS), RPMI-1640 media, rhodamine B-labeled dextran (MW: 10,000 Da) and Dulbecco's phosphate buffered saline (DPBS) were purchased from Invitrogen (Carlsbad, Calif.). All solvents were of reagent grade and used as purchased. Chromatography grade solvents were used for HPLC without purification.

PEGtides were purified on an Alliance reverse-phase high-performance liquid chromatography (RP-HPLC) system (Waters, Mass.) using a Symmetry C18 column (4.6× 150 mm, 100 Å, particle size 5 μm). Following mobile phase was used: solvent A, 0.05% aqueous TFA; and solvent B, acetonitrile containing 0.05% TFA. A linear gradient of 95% to 70% of A was applied for 60 min at a flow rate of 1 mL/min. The UV absorptions were monitored at 220 and 250 nm, whereas fluorescence detector was set with excitation and emission wavelengths of 492 and 518 nm, respectively. The dendrons and there derivatives were quantified on a F-7000 fluorescence spectrophotometer (HITACHI, Japan). Mass spectra were acquired on an ABI-MDS SCIEX 4800 matrix-assisted laser desorption/ionisation-time of flight (MALDI-TOF/TOF) mass spectrometer (AB Sciex, Foster City, Calif.). Sample solutions (2 μL) were mixed with matrix solution (20 μL, 20 mg/mL sinapinic acid in 50% aqueous acetonitrile containing 0.1% TFA). This mixture (1 μL) was spotted onto sample holder and dried under a gentle stream of argon at room temperature. All spectra were recorded in positive mode using a linear acquisition method. The dynamic light scattering (DLS) experiments were performed on a Wyatt Dynapro Titan instrument (Wyatt Technology, Santa Barbara, Calif.) with sample concentration of 1 mg/mL. Data were acquired at 4° C. over 10 seconds, repeated 10 times and then averaged.

Example 1A

Synthesis and Characterization of Generation 3.0 (G3.0) PEGtide Dendron (FIG. 1)

(1) 100 mg of Fmoc-Cys(Trt)-Wang Resin (0.65 mmol/g) was weighed and transferred into a PD-10 column. The resin was swollen in N,N-dimethylformamide (DMF), dichloromethane (DCM) and DMF for 10 minutes each.

(2) The resin was drained, 10 ml piperidine/DMF (1/4 of volume ratio) was added, and resin was placed on shaker for 20 minutes.

(3) The resin was washed with DMF 6-times and a small amount of resin was used for Kaiser test. Moved to next cycle if the color of resin turned blue, otherwise repeated step (2).

(4) 3.1 mg of Fmoc-β-Ala-OH (0.01 mmol), 4.1 mg 1-hydroxybenzotrizole (HOBT) (0.03 mmol), and 15.6 mg Benzotriazole-1-yl-oxy-tris-pyrrolidino-phosphonium hexafluorophosphate (PyBOP) (0.03 mmol) were dissolved in 0.1 ml of DMF. The mixture in DMF was added to the PD-10 column containing the resin, and then 5.0 μl N,N-diisopropylethylamine (DIEA) (0.03 mmol) was added and the column was placed on shaker for 4 hours.

(5) The resin was washed with DMF for 6-times and column was drained followed by Kaiser test.

(6) 61.3 μl of acetic anhydride (0.65 mmol) and DIEA (32.2 μl, 0.195 mmol) were transferred to the column, and column was placed on shaker for 2 hours.

(7) The resin was washed with DMF for 3-times and Kaiser test was performed. Moved to next step if the resin was colorless, otherwise repeated step (6).

(8) Repeated steps (2) and (3).

(9) 17.7 mg of Fmoc-Lys(Fmoc)-OH (0.03 mmol), 4.1 mg of HOBT (0.03 mmol), and 15.6 mg of PyBOP (0.03 mmol) were dissolved into 0.1 ml of DMF solution. The DMF mixture was transferred to the column and 5.0 μl of DIEA (0.03 mmol) was added followed by shaking for 4 hours.

(10) The resin was washed with DMF and Kaiser test was performed. If the resin was colorless, continued to step (11); otherwise, repeated step (9).

(11) Repeated steps (2) and (3).

(12) 18.7 mg of Fmoc-β-Ala-OH (0.06 mmol), 8.1 mg of HOBT (0.06 mmol), and 31.2 mg of PyBOP (0.06 mmol) were dissolved into 0.1 ml of DMF solution. The DMF solution was transferred to the reaction column and 9.9 μl of DIEA (0.06 mmol) was added followed by continuous shaking for 4 hours.

(13) The resin was washed with DMF and Kaiser test was performed. If the resin was colorless, continued to step (14); otherwise, repeated step (12).

(14) Repeated steps (2) and (3).

(15) 50.4 mg of N-Fmoc-amide-dPEG$_{12}$™-acid (Quanta Biodesign Cat. No. 10283) (0.06 mmol), 8.1 mg of HOBT (0.06 mmol), and 31.2 mg of PyBOP (0.06 mmol) were dissolved into 0.1 ml of DMF solution. The DMF solution was transferred to the reaction column and 9.9 μl of DIEA (0.06 mmol) was added, followed by shaking for 4 hours.

(16) The resin was washed with DMF and Kaiser test was performed. If the resin was colorless, continued to step (17); otherwise, repeated step (15).

(17) Repeated steps (2) and (3).

(18) 35.4 mg of Fmoc-Lys(Fmoc)-OH (0.06 mmol), 8.1 mg of HOBT (0.06 mmol), and 31.2 mg of PyBOP (0.06 mmol) were dissolved into 0.1 ml of DMF. The DMF solution was transferred to the reaction column and 9.9 μl of DIEA (0.06 mmol) was added, followed by shaking for 4 hours.

(19) The resin was washed with DMF and Kaiser test was performed. If the resin was colorless, continued to step (20); otherwise, repeated step (18).

(20) Repeated steps (2) and (3).

(21) 37.4 mg of Fmoc-β-Ala-OH (0.12 mmol), 16.2 mg of HOBT (0.12 mmol), and 62.4 mg of PyBOP (0.12 mmol) were dissolved into 0.1 ml of DMF. The DMF solution was transferred to the reaction column and 19.8 μl of DIEA (0.12 mmol) was added followed by shaking for 4 hours.

(22) The resin was washed with DMF and Kaiser test was performed. If the resin was colorless, continued to step (23); otherwise, repeated step (21).

(23) Repeated steps (2) and (3).

(24) 100.8 mg of N-Fmoc-amide-dPEG$_{12}$™-acid (Quanta Biodesign Cat. No. 10283) (0.12 mmol), 16.2 mg of HOBT (0.12 mmol), and 62.4 mg of PyBOP (0.12 mmol) were dissolved into 0.1 ml of DMF. The DMF solution was transferred to the reaction column and 19.8 μl of DIEA (0.12 mmol) was added, followed by continued shaking for 4 hours.

(25) The resin was washed with DMF and Kaiser test was performed. If the resin was colorless, continued to step (26); otherwise, repeated step (24).

(26) Repeated steps (2) and (3).

(27) 70.9 mg of Fmoc-β-Ala-OH (0.12 mmol), 16.2 mg of HOBT (0.12 mmol), and 62.4 mg of PyBOP (0.12 mmol) were dissolved into 0.1 ml of DMF. The DMF solution was added to the reaction column and 19.8 μl of DIEA (0.12 mmol) was added, followed by continued shaking for 4 hours.

(28) The resin was washed with DMF and Kaiser test was performed. If the resin was colorless, continued to step (29); otherwise, repeated step (27).

(29) Repeated steps (2) and (3).

(30) 74.7 mg of Fmoc-β-Ala-OH (0.24 mmol), 32.4 mg of HOBT (0.24 mmol), and 124.9 mg of PyBOP (0.24 mmol) were dissolved into 0.1 ml of DMF. The DMF solution was added to the reaction column and 39.7 μl of DIEA (0.24 mmol) was added, followed by continued shaking for 4 hours.

(31) The resin was washed with DMF and Kaiser test was performed. If the resin was colorless, continued to step (32); otherwise, repeated step (30).

(32) Repeated steps (2) and (3).

(33) 201.6 mg of N-Fmoc-amide-dPEG$_{12}$™-acid (Quanta Biodesign Cat. No. 10283) (0.24 mmol), 32.4 mg of HOBT (0.24 mmol), and 124.9 mg of PyBOP (0.24 mmol) were dissolved into 0.1 ml of DMF. The DMF solution was added to the reaction column and 39.7 μl of DIEA (0.24 mmol) was added, followed by shaking for 4 hours.

(34) The resin was washed with DMF and Kaiser test was performed. If the resin was colorless, continued to step (35); otherwise, repeated step (33).

(35) The resin was washed with DCM and dried under vacuum.

(36) The 10 ml of following cleavage cocktail solution was added to the reaction column, followed by shaking for 2 hours. Trifluoroacetic Acid (TFA)/1,2-Ethanedithiol/Water/Triisopropylsilane=94/2.5/2.5/1.

(37) The resin was filtered and the filtrate was collected, concentrated, and precipitated from cold ether with stirring. The precipitate was collected by centrifugation (3,000 rpm for 2 minutes).

(38) The precipitate was dissolved in DMF and step 37 (concentration followed by precipitation) was repeated 3-times.

(39) The precipitate was dried overnight under vacuum.

Figure 2:
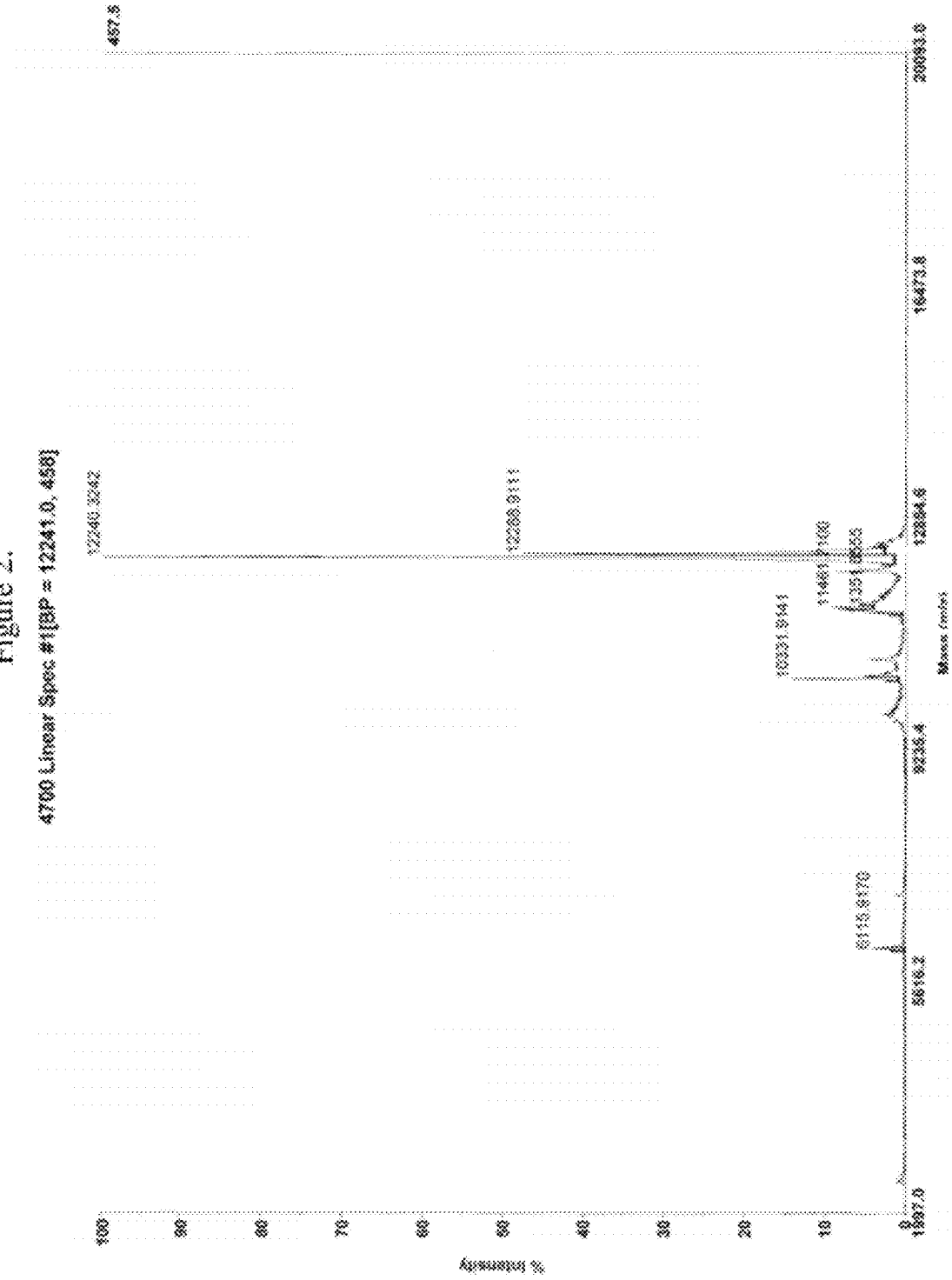
FIG. 2 is a MALDI-TOF spectrum of a generation 3.0 (G3.0) PEGtide dendron: C-A-K-{A-PEG-K-[A-PEG-K-(A-PEG)$_2$]$_2$}$_2$.

(40) MALDI-TOF analysis. The sample solution (1 mg/ml) was prepared in aqueous solution containing 0.1% TFA. The 2 µl of sample solution was taken and mixed with 21 µl of sinapinic acid matrix solution. The 1 µl of this mixture was spotted on the Opti-TOF™ 384 Well Insert Plate for MALDI-TOF (FIG. 2). The observed and calculated molecular weights were 12240.3 D and 12258.5 D, respectively.

(41) DLS analysis

Figure 3:
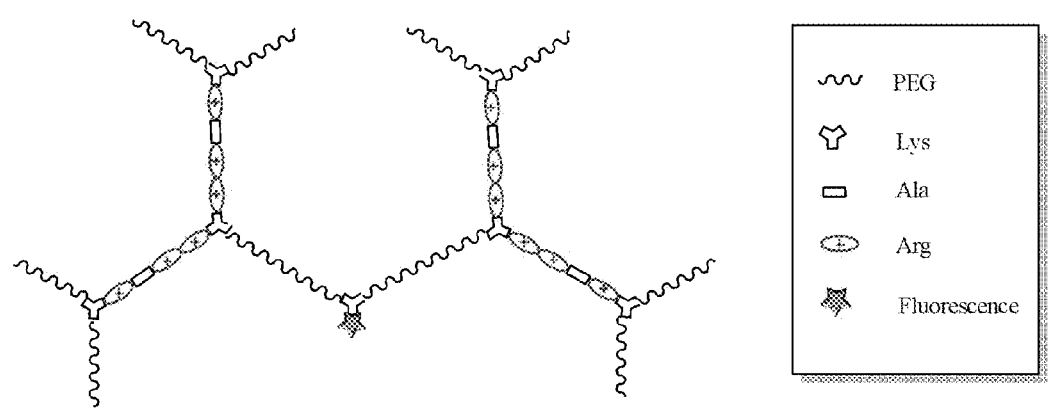
FIG. 3 shows the results of dynamic light scattering (DLS) analysis of a generation 3.0 (G3.0) PEGtide dendron, which shows that the dendron has a radius of 53.9 nm.

The sample solution (1 mg/ml) was prepared in water and used for DLS studies. The radii of PEGTide dendron G3.0 was found as 53.9 nm (FIG. 3).

Example 1B

Figure 4:
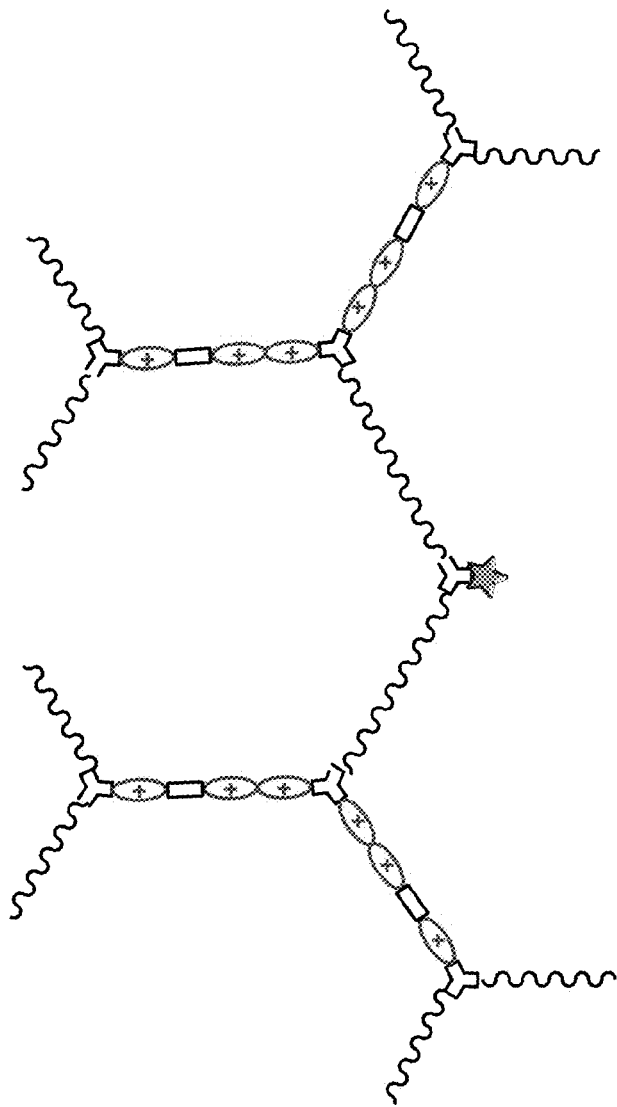
FIG. 4 depicts the structure of 5-carboxyfluorescein (FAM) and arginine-containing PEGTide dendron G3.0.

Synthesis of PEGtide Dendron G3.0 Containing Arginine and 5-Carboxyfluorescein (FAM) (FIG. 4)

(1) 200 mg of Fmoc-β-Ala-Wang Resin (0.36 mmol/g) was weighed and transferred into PD-10 column. The resin was swollen in DMF two times for 15 minutes.

(2) The resin was drained and then 10 ml of piperidine/DMF (1/4 of volume ratio) was added, followed by shaking for 20 minutes.

(3) The resin was washed with DMF 4-times and a small amount of resin was taken out for Kaiser test. If the color of the resin was blue, continued to the next step; otherwise, repeated step (2).

(4) 14.5 mg of Fmoc-Lys (FAM)-OH (0.02 mmol), 10.8 mg of 1-hydroxybenzotrizole (HOBT) (0.08 mmol), and 41.6 mg of benzotriazole-1-yl-oxy-tris-pyrrolidino-phosphonium hexafluorophosphate (PyBOP) (0.08 mmol) were dissolved into 5.0 ml of DMF. The DMF solution was added to the PD-10 column containing the resin and 26.4 µl of N,N-diisopropyl-ethylamine (DIEA) (0.16 mmol) was added, and column was placed on a shaker for 4 hours.

(5) The resin was washed with DMF 2-times and a small amount of resin was taken out for Kaiser test. If the resin turned light blue, moved to the next step.

(6) The 67.9 µl of acetic anhydride (0.72 mmol) and 35.7 µl of DIEA (0.216 mmol) was added to the reaction column, followed by shaking for 2 hours.

(7) The resin was washed with DMF 2-times and Kaiser test was performed. If the resin was colorless, continued to next step; otherwise, repeated the step (6).

(8) Repeated steps (2) and (3).

(9) 46.1 mg of N-Fmoc-amide-dPEG$_6$™-acid (Quanta Biodesign Cat. No. 10063) (0.08 mmol), 10.8 mg of HOBT (0.08 mmol), and 41.6 mg of PyBOP (0.08 mmol) were dissolved into 5.0 ml of DMF. The DMF solution was transferred to the reaction column and 26.4 µl of DIEA (0.16 mmol) was added, followed by continued shaking for 4 hours.

(10) Repeated steps (7), (2) and (3)

(11) 47.3 mg of Fmoc-Lys(Fmoc)-OH (0.08 mmol), 10.8 mg of HOBT (0.08 mmol), and 41.6 mg of PyBOP (0.08 mmol) were dissolved into 5.0 ml of DMF. The DMF solution was transferred to the reaction column and 26.4 µl of DIEA (0.16 mmol) was added, followed by continued shaking for 4 hours.

(12) Repeated steps (7), (2) and (3)

(13) 49.8 mg of Fmoc-β-Ala-OH (0.16 mmol), 21.6 mg of HOBT (0.16 mmol), and 83.3 mg of PyBOP (0.16 mmol) were dissolved into 5.0 ml of DMF. The DMF solution was transferred to the reaction column and 52.9 µl of DIEA (0.32 mmol) was added, followed by continued shaking for 4 hours.

(14) Repeated steps (7), (2) and (3)

(15) 92.1 mg of N-Fmoc-amide-dPEG$_6$™-acid (Quanta Biodesign Cat. No. 10063) (0.16 mmol), 21.6 mg of HOBT (0.16 mmol), and 83.3 mg of PyBOP (0.16 mmol) were dissolved into 5.0 ml of DMF. The DMF solution was transferred to the reaction column and 52.9 µl of DIEA (0.32 mmol) was added, followed by shaking for 4 hours.

(16) Repeated steps (7), (2) and (3)

(17) 94.5 mg of Fmoc-Lys(Fmoc)-OH (0.16 mmol), 21.6 mg of HOBT (0.16 mmol), and 83.3 mg of PyBOP (0.16 mmol) were dissolved into 5.0 ml of DMF. The DMF solution was added to the reaction column and 52.9 µl of DIEA (0.32 mmol) was added, followed by shaking for 4 hours.

(18) Repeated steps (7), (2) and (3)

(19) 99.6 mg of Fmoc-β-Ala-OH (0.32 mmol), 43.2 mg of HOBT (0.32 mmol), and 166.5 mg of PyBOP (0.32 mmol) were dissolved into 5.0 ml of DMF. The DMF solution was added to the reaction column and 105.8 µl of DIEA (0.64 mmol) was added, followed by shaking for 4 hours.

(20) Repeated step (7).

(21) The resin was washed with DCM and dried under vacuum. The resin containing 0.002 mmol of dendron was weighed and used for following experiments.

(22) Repeated steps (2) and (3).

(23) 20.8 mg of Fmoc-Arg(Pbf)-OH (0.032 mmol), 4.4 mg of HOBT (0.032 mmol), and 16.6 mg of PyBOP (0.032 mmol) were dissolved into 0.5 ml of DMF. The DMF solution was transferred to the reaction column and 10.6 µl of DIEA (0.064 mmol) was added, followed by shaking for 4 hours.

(24) Repeated steps (7), (2) and (3)

(25) Repeated step (23)

(26) Repeated steps (7), (2) and (3)

(27) 9.96 mg of Fmoc-β-Ala-OH (0.032 mmol), 4.32 mg of HOBT (0.032 mmol), and 16.65 mg of PyBOP (0.032 mmol) were dissolved into 0.5 ml of DMF. The DMF solution was added to the reaction column and 10.6 µl of DIEA (0.064 mmol) was added and placed on shaker for overnight period.

(28) Repeated steps (7), (2) and (3)

(29) Repeated step (23)

(30) Repeated steps (7), (2) and (3)

(31) Repeated step (27)

(32) Repeated steps (7), (2) and (3)

(33) 18.9 mg of Fmoc-Lys(Fmoc)-OH (0.032 mmol), 4.4 mg of HOBT (0.032 mmol), and 16.6 mg of PyBOP (0.032 mmol) were dissolved into 0.5 ml of DMF. The DMF solution was added to the reaction column and 10.6 µl of DIEA (0.064 mmol) was added, followed by shaking for 4 hours.

(34) Repeated steps (7), (2) and (3)

(35) 19.9 mg of Fmoc-β-Ala-OH (0.064 mmol), 8.7 mg of HOBT (0.064 mmol), and 33.3 mg of PyBOP (0.064 mmol) were dissolved into 0.5 ml of DMF. The DMF solution was added to the reaction column and 21.2 µl of DIEA (0.128 mmol) was added, followed by overnight shaking.

(36) Repeated steps (7), (2) and (3)

(37) 36.8 mg of N-Fmoc-amide-dPEG$_6$™-acid (Quanta Biodesign Cat. No. 10063) (0.064 mmol), 8.7 mg of HOBT (0.064 mmol), and 33.3 mg of PyBOP (0.064 mmol) were dissolved into 0.5 ml of DMF. The DMF solution was transferred to the reaction column and 21.2 µl of DIEA (0.128 mmol) was added, followed by shaking for 4 hours.

(38) Repeated steps (7), (2) and (3)

(39) The resin was washed with DCM and dried under vacuum.

(40) The 10 ml of following cleavage cocktail solution was added into the reaction column, followed by shaking for 2 hours. Trifluoroacetic Acid (TFA)/Water/Triisopropylsilane=95/2.5/2.5.

(41) The resin was filtered and filtrate was collected, which was concentrated and then precipitated from cold ether with stirring. The precipitate was collected by centrifugation (3,000 rpm for 2 minutes).

(42) The precipitate was dissolved in DMF and reprecipitated from cold ether as described in step (32). This process was repeated 3-times.

(43) The precipitate was dried under vacuum overnight.

(44) MALDI-TOF analysis"

Figure 5:
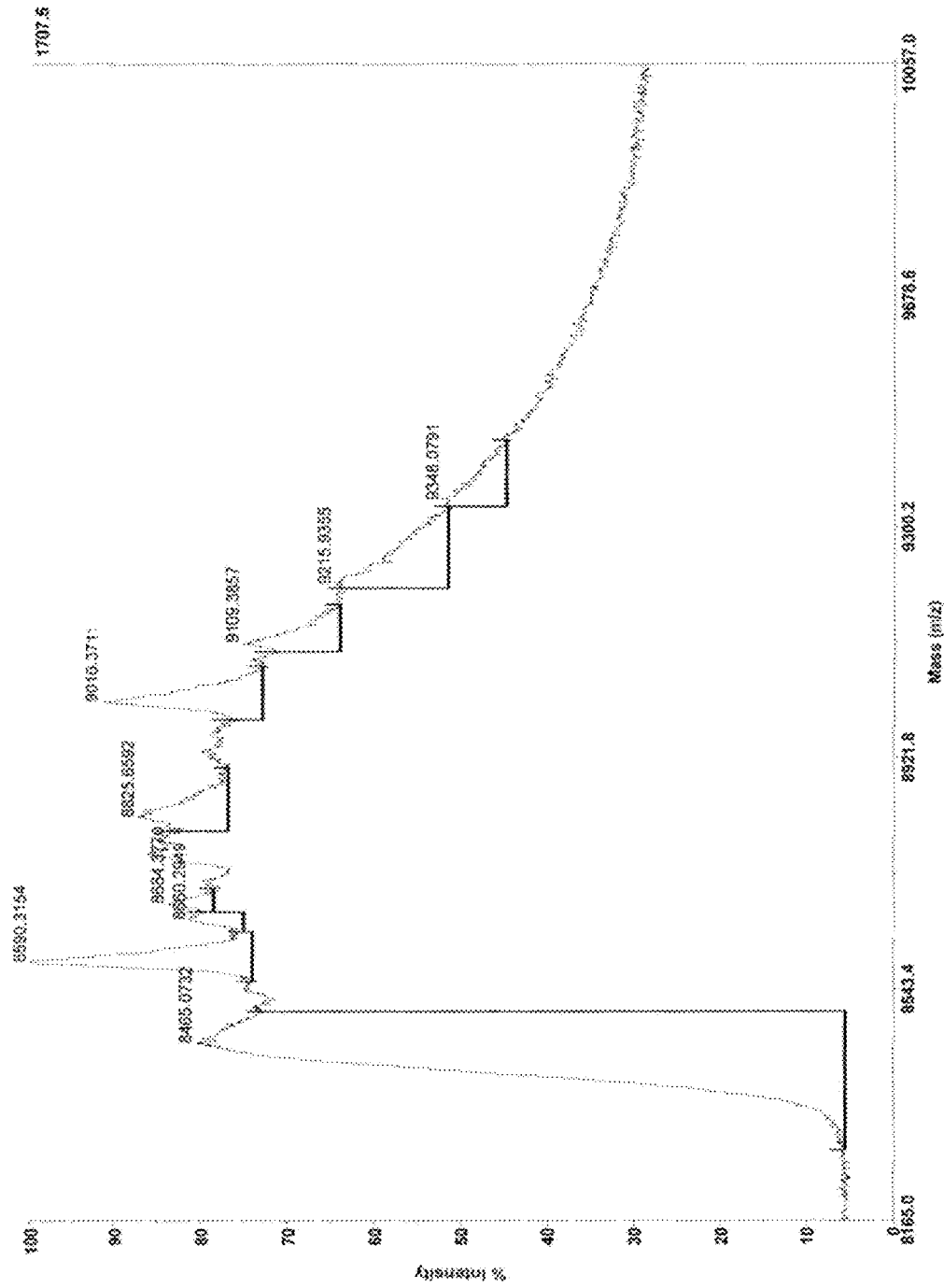
FIG. 5 is a MALDI-TOF spectrum of 5-carboxyfluorescein (FAM) and arginine-containing PEGTide dendron G3.0 with following structure: A-K(FAM)-PEG-K-{A-PEG-K-[A-R-R-A-R-A-K-(A-PEG)$_2$]$_2$}$_2$.

The sample solution was prepared (1 mg/ml) in water containing 0.1 TFA %. The 2 µl of sample solution was mixed with 21 µl of sinapinic acid matrix solution. 1 µl of this mixture was spotted on the Opti-TOF™ 384 Well Insert Plate for MALDI-TOF (FIG. 5). The observed and calculated molecular weights were 8590.3 D and 8598.0 D, respectively.

Example 1C

Figure 6:
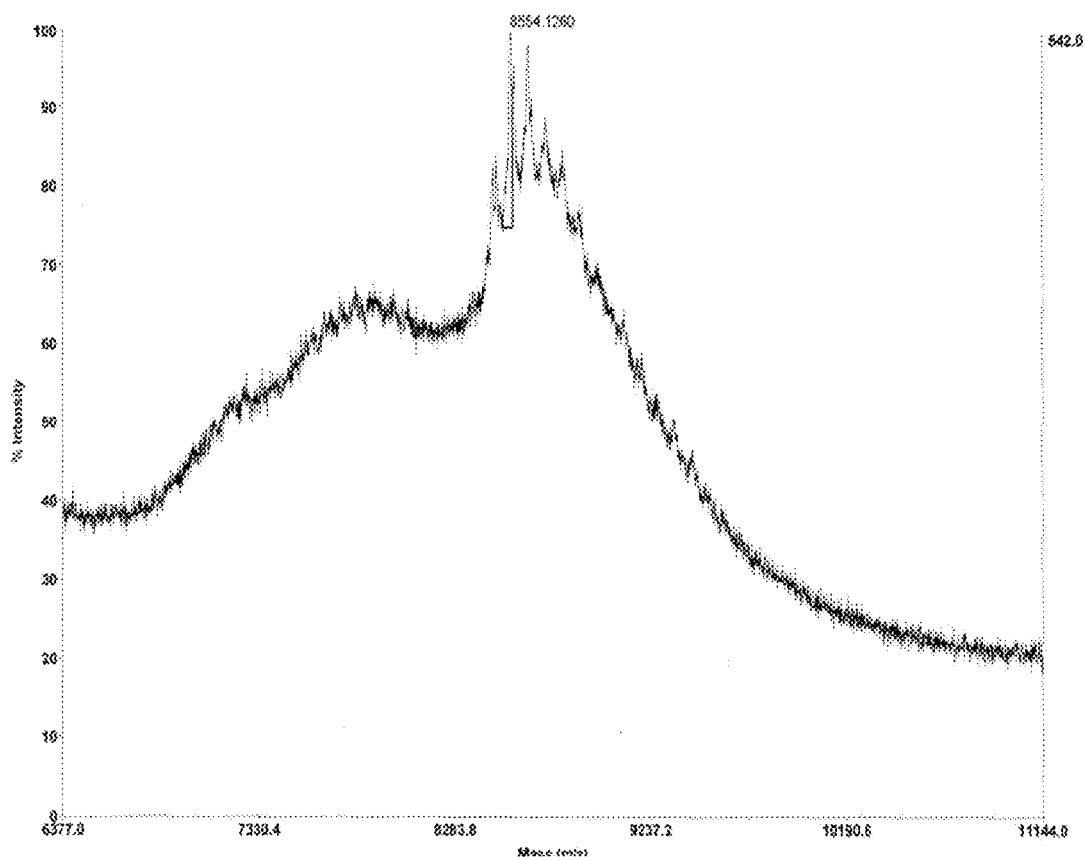
FIG. 6 illustrates the structure of DV3-containing tetravalent PEGTide dendron G2.0.

Synthesis of dv3-Containing Tetravalent PEGtide Dendron g2.0 (FIG. 6)

(1) Steps (1) to (20) described in EXAMPLE 1B were repeated.

(2) The resin was washed with DCM and dried under vacuum. The resin containing 0.01 mmol of dendron was weighed and swollen with DMF 2-times for 15 minutes each. Following experiments were carried out.

(3) The resin was drained and 10 ml of piperidine/DMF (1/4 of volume ratio) was added, followed by shaking for 20 minutes.

(4) The resin was washed with DMF 4-times and a small amount of resin was taken out for Kaiser test. If the color of the resin turned blue, continued to the next step; otherwise, repeated step (3).

(5) 92.1 mg of N-Fmoc-amide-dPEG$_6$™-acid (Quanta Biodesign Cat. No. 10063) (0.16 mmol), 21.6 mg HOBT (0.16 mmol), and 83.2 mg of PyBOP (0.16 mmol) were dissolved into 2.0 ml of DMF. The DMF solution was added to the reaction column and 52.9 µl of DIEA (0.32 mmol) was added, followed by shaking for 4 hours.

(6) The resin was washed with DMF for 2-times and Kaiser test was per-formed. If the resin was colorless, continued to next step; otherwise, repeated step (5).

(7) Repeated steps (3) and (4).

(8) 47.6 mg Fmoc-Gly-OH (0.16 mmol), 21.6 mg HOBT (0.16 mmol), and 83.2 mg PyBOP (0.16 mmol) were dissolved into 2.0 ml of DMF. The DMF solution was transferred to the reaction column and 52.9 µl of DIEA (0.32 mmol) was added, followed by shaking for 4 hrs.

(9) Repeated steps (6), (3) and (4).

(10) 75.0 mg of Fmoc-Lys(Boc)-OH (0.16 mmol), 21.6 mg of HOBT (0.16 mmol), and 83.2 mg of PyBOP (0.16 mmol) were dissolved into 2.0 ml of DMF. The DMF solution was transferred to the reaction column and 52.9 µl of DIEA (0.32 mmol) was added, followed by shaking for 4 hours.

(11) Repeated steps (6), (3) and (4).

(12) 65.8 mg of Fmoc-Asp(OtBu)-OH (0.16 mmol), 21.6 mg of HOBT (0.16 mmol), and 83.2 mg of PyBOP (0.16 mmol) were dissolved into 2.0 ml of DMF. The DMF solution was added to the reaction column and 52.9 µl of DIEA (0.32 mmol) was added, followed by shaking for 4 hours.

(13) Repeated steps (6), (3) and (4).

(14) 54.0 mg of Fmoc-Pro-OH (0.16 mmol), 21.6 mg of HOBT (0.16 mmol), and 83.2 mg of PyBOP (0.16 mmol) were dissolved into 2.0 ml of DMF. The DMF solution was transferred to the reaction column and 52.9 µl of DIEA (0.32 mmol) was added, followed by shaking for 4 hours.

(15) Repeated steps (6), (3) and (4).

(16) 103.8 mg of Fmoc-Arg(Pbf)-OH (0.16 mmol), 21.6 mg of HOBT (0.16 mmol), and 83.2 mg of PyBOP (0.16 mmol) were dissolved into 2.0 ml of DMF. The DMF solution was transferred to the reaction column and 52.9 µl of DIEA (0.32 mmol) was added, followed by shaking for 4 hours.

(17) Repeated steps (6), (3) and (4).

(18) 99.2 mg of Fmoc-His(Trt)-OH (0.16 mmol), 21.6 mg of HOBT (0.16 mmol), and 83.2 mg of PyBOP (0.16 mmol) were dissolved into 2.0 ml of DMF. The DMF solution was transferred to the reaction column and 52.9 µl of DIEA (0.32 mmol) was added, followed by shaking for 4 hours.

(19) Repeated steps (6), (3) and (4).

(20) 84.3 mg of Fmoc-Trp(Boc)-OH (0.16 mmol), 21.6 mg of HOBT (0.16 mmol), and 83.2 mg of PyBOP (0.16 mmol) were dissolved into 2.0 ml of DMF. The DMF solution was added to the reaction column and 52.9 µl of DIEA (0.32 mmol) was added, followed by shaking for 4 hours.

(21) Repeated steps (6), (3) and (4).

(22) 61.3 mg of Fmoc-Ser(tBu)-OH (0.16 mmol), 21.6 mg of HOBT (0.16 mmol), and 83.2 mg of PyBOP (0.16 mmol) were dissolved into 2.0 ml of DMF. The DMF solution was added to the reaction column and 52.9 µl of DIEA (0.32 mmol) was added, followed by shaking for 4 hours.

(23) Repeated steps (6), (3) and (4).

(24) 49.8 mg of Fmoc-Ala-OH (0.16 mmol), 21.6 mg of HOBT (0.16 mmol), and 83.2 mg of PyBOP (0.16 mmol) were dissolved into 2.0 ml of DMF. The DMF solution was transferred to the reaction column and 52.9 µl of DIEA (0.32 mmol) was added, followed by shaking for 4 hours.

(25) Repeated steps (6), (3) and (4).

(26) 47.6 mg of Fmoc-Gly-OH (0.16 mmol), 21.6 mg of HOBT (0.16 mmol), and 83.2 mg of PyBOP (0.16 mmol) were dissolved into 2.0 ml of DMF. The DMF solution was transferred to the reaction column then 52.9 µl of DIEA (0.32 mmol) was added, followed by shaking for 4 hours.

(27) Repeated steps (6), (3) and (4).

(28) 56.5 mg of Fmoc-Leu-OH (0.16 mmol), 21.6 mg of HOBT (0.16 mmol), and 83.2 mg PyBOP (0.16 mmol) were dissolved into 2.0 ml of DMF solution. The DMF solution was added to the reaction column and add 52.9 µl of DIEA (0.32 mmol) was added, followed by shaking for 4 hours.

(29) Repeated step (6), (3) and (4).

(30) The resin was washed with DCM and dried under vacuum.

(31) The 10 ml of following cleavage cocktail solution was added into the reaction column, followed by shaking for 2 hours. Trifluoroacetic Acid (TFA)/Water/Triisopropylsilane=95/2.5/2.5.

(32) The resin was filtered and filtrate was collected, which was concentrated and precipitated from cold ether with stirring. The precipitate was collected by centrifugation (3,000 rpm for 2 minutes).

(33) The precipitate was dissolve in DMF and re-precipitated as described in step (32). This process was repeated 3-times.

(34) The precipitate was dried under vacuum overnight.

(35) MALDI-TOF analysis.

Figure 7:
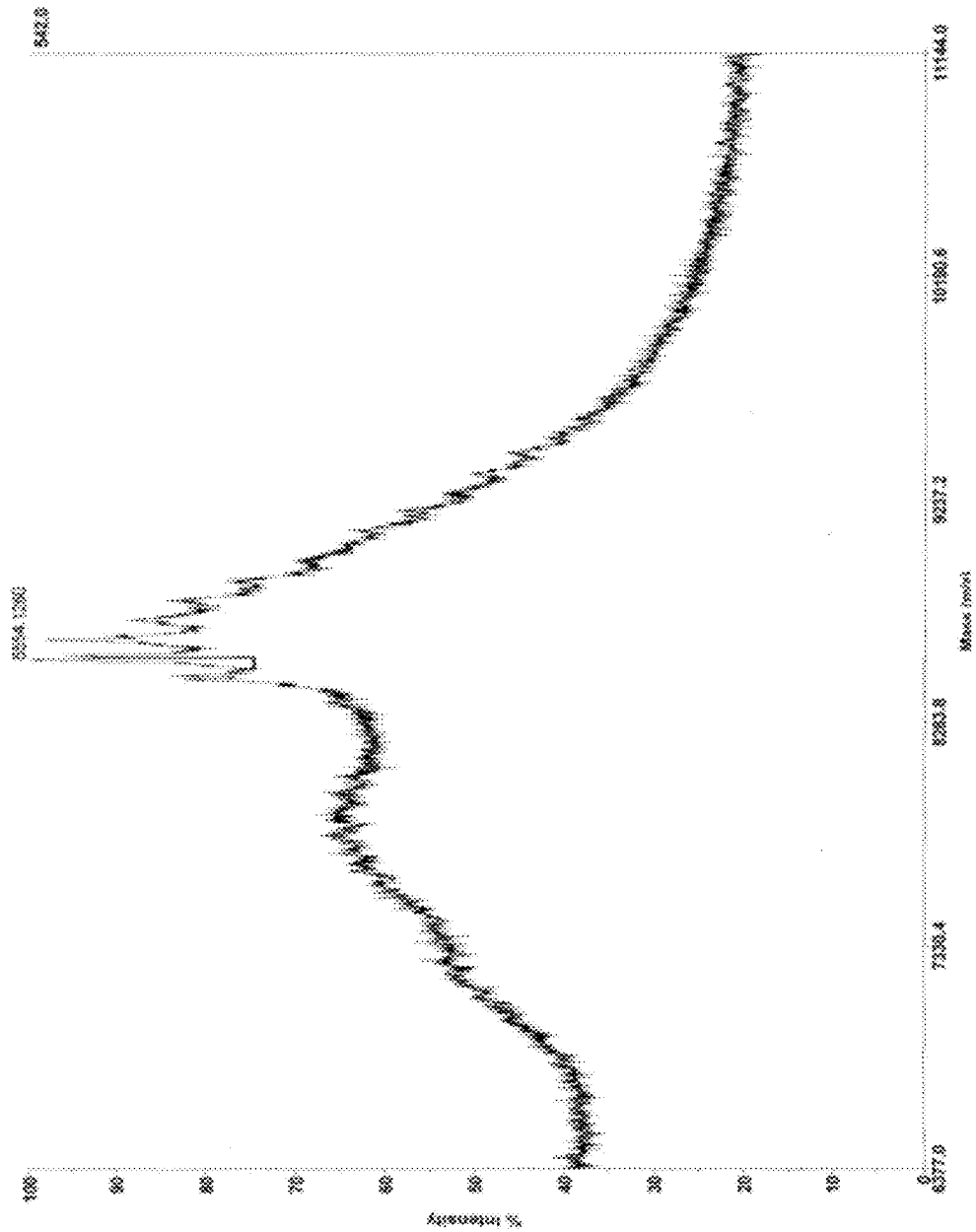
FIG. 7 is the MALDI-TOF spectrum of DV3-containing tetravalent PEGTide dendron G2.0 with following structure: A-K(FAM)-PEG-K-[A-PEG-K-(A-PEG-G-K-D-P-R-H-W-S-A-G-L)$_2$]$_2$.

The sample solution was prepared (1 mg, m/1) in aqueous solution containing 0.1 TFA %. The 2 μl of sample solution was taken and mixed with 21 μl of sinapinic acid matrix solution. The 1 μl of this mixture was spotted on the Opti-TOF™ 384 Well Insert Plate for MALDI-TOF (FIG. 7). The observed and calculated molecular weights were 8554.1 D and 8554.5 D, respectively.

Example 1D

Synthesis of A-K(5-FAM)-PEG$_6$-Fmoc (1)

The derivative (1) was synthesized on Fmoc-β-Ala-Wang Resin (loading capacity: 0.36 mmole/g) in following steps.

(1) 0.1 g of Wang resin was swollen in DMF for 1 hr and washed with DMF (3×3 mL).

(2) The N-terminal Fmoc group was removed using piperidine/DMF (1:4 v/v) (2×4 mL, 10 min each), followed by washing with DMF (3×4 mL).

(3) Fmoc-Lys (5-FAM)-OH (7.3 mg, 0.01 mmole) was activated with PyBOP (20.8 mg, 0.04 mmole) and HOBT (5.4 mg, 0.04 mmole) in DMF (2.0-3.0 mL) for 20 min, mixed with DIPEA (13.2 μL, 0.08 mmole), and transferred to PD-10 column for coupling. The column was placed on a shaker for 4 hrs.

(4) The resin was washed with DMF (3×4 mL) and treated with acetic anhydride (24.5 μL, 0.26 mmole) and DIPEA (17.2 μL, 0.10 mmole) in DMF (2.0 mL) for 0.5 hr.

(5) The step 2 was repeated to remove terminal Fmoc group with piperidine/DMF.

(6) To couple PEG, step 3 was repeated using Fmoc-PEG$_6$-OH (4 equiv., 23.0 mg, 0.04 mmole), PyBOP (20.8 mg, 0.04 mmole), HOBT (5.4 mg, 0.04 mmole), DMF (2.0-3.0 mL), and DIPEA (8 equiv., 13.2 μL, 0.08 mmole).

(7) The visual Kaiser test was used to monitor completion of each deprotection and coupling steps (Kutscher, H. L., *International Journal of Pharmaceutics* 402, 64-71, (2010)) few resin beads were taken out in a vial and 2 drops of each ninhydrin, phenol and pyridine were added to it. The vial was heated at 110° C. for 3 min. Finally the resin was washed and dried in vacuum (108.1 mg resin was obtained, 8.1 mg mass gain: 98.6%). MALDI-TOF: MW: calcd. 1132.45 Da. found 1130.38 Da.

Synthesis of PEGtide Dendrons G1.0-G4.0. PEDtide Dendrons G1.0-4.0 were Synthesized from (1) as Follows.

G1.0. To obtain PEGtide dendron G1.0, three cycles of step 2, 3, and 4 (described above) were repeated to couple Fmoc-Lys(Fmoc)-OH (23.6 mg, 0.04 mmole), Fmoc-β-Ala-OH (24.9 mg, 0.08 mmole), and Fmoc-PEG$_6$-OH (46.1 mg, 0.08 mmole), respectively. About 4 equiv. of PyBOP and HOBT, and 8 equiv. of DIPEA were used in each coupling step. At the end of these coupling cycles, step 2 was repeated one more time to remove the terminal Fmoc groups. The visual Kaiser test was used to monitor completion of each deprotection and coupling steps (step 7). The resin was washed with DMF (2×3 mL), DCM (2×3 mL), and methanol (2×3 mL) and dried overnight under vacuum to obtain the resin-bound PEGtide dendrons G1.0 (Yield. 118.1 mg, 18.1 mg mass gain, 91%). Finally, the PEGtides were cleaved from support by treating with a cocktail of TFA/water/triisopropylsilane (TIS) (95/2.5/2.5 v/v/v) for 2 hrs. The cleavage cocktail was removed under vacuum, and the crude dendrons were stored at −20° C. and further purified by HPLC. MALDI-TOF: MW, calcd. 1851.68 Da. found 1849.72 Da.

G2.0-4.0. The PEGtide dendrons G2.0 were obtained from resin-bound Fmoc-protected PEGtide dendrons G1.0 (2) by using a process similar to describe above for the synthesis of G1.0. Similarly G3.0 were obtained from resin-bound Fmoc-protected G2.0 (3) and G4.0 were obtained from resin-bound Fmoc-protected G3.0 (4). The yields of support bound PEGtide dendrons G2.0-4.0 were as follows: G2.0: 137.5 mg (37.5 mg mass gain, 87%); G3.0: 169.3 mg (69.3 mg mass gain, 77%); and G4.0: 207.8 mg (107.8 mg mass gain, 59%). MALDI-TOF: MW: G2.0: calcd. 3733.06 Da. found 3730.31 Da; G3.0: calcd. 7497.30 Da. found 7486.30 Da; and G4.0: calcd. 15023.77 Da. found 15022.1 Da.

Synthesis and Characterization of Pegtide Dendrons G1.0-4.0

Figure 9A:
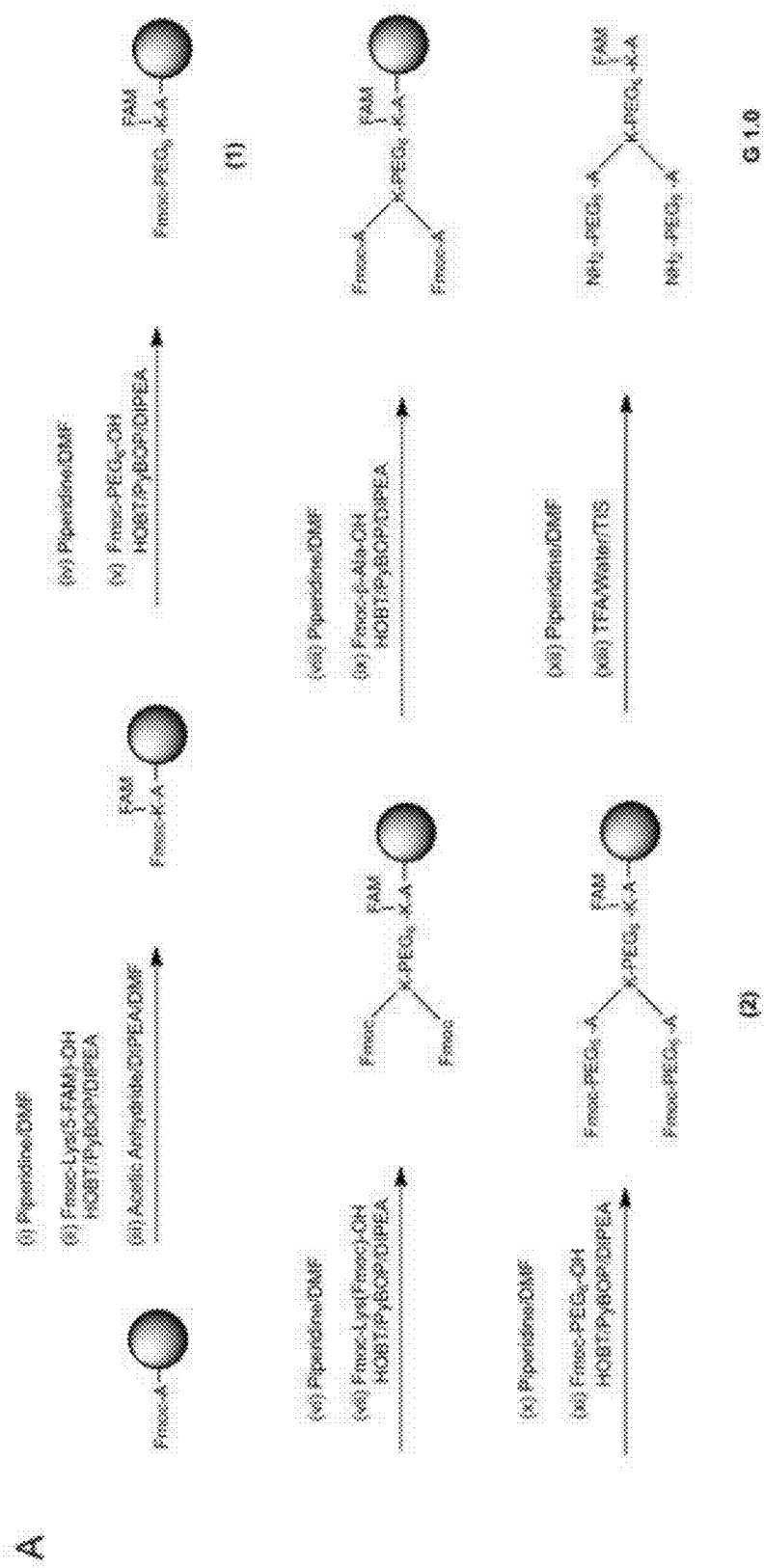
(FIG. 9A) G1.0.

PEGtide dendrons of different generations, G1.0-4.0, were synthesized by sequentially assembling Fmoc-K (Fmoc)-OH, Fmoc-β-A-OH, and Fmoc-PEG$_6$-OH on a solid support. The Fmoc approach of solid-phase peptide synthesis (SPPS) and a divergent strategy was used to obtain PEGtide dendrons, G1.0-4.0. Briefly, Fmoc-K(5-FAM)-OH was coupled to Fmoc-β-A-Wang resin to obtain resin-bound A-K(5-FAM)-PEG$_6$-Fmoc (1) (FIG. 9A). The 5-FAM-labeled lysine (K) was incorporated to detect dendrons in biological assays. The synthesis of PEGtide dendron G1.0 was initiated by coupling Fmoc-K(Fmoc)-OH to (1). In the next step, Fmoc-β-A-OH was coupled to α-ε-amino groups of lysine. Finally, monodisperse Fmoc-PEG$_6$-OH was coupled to both alanine (A) moieties to obtain resin-bound G1.0 dendrons (2). The G1.0 dendrons were obtained after deprotection of terminal Fmoc groups and cleavage from support. Usually large excess of amino acid/PEG was used to drive reaction to completion, and HOBT and PyBOP were used for coupling due to their high reactivity and chiral stability of benzotriazoyl esters of amino acid/peptide. Relatively longer durations were used for coupling and deprotection reactions.

Figure 9B:
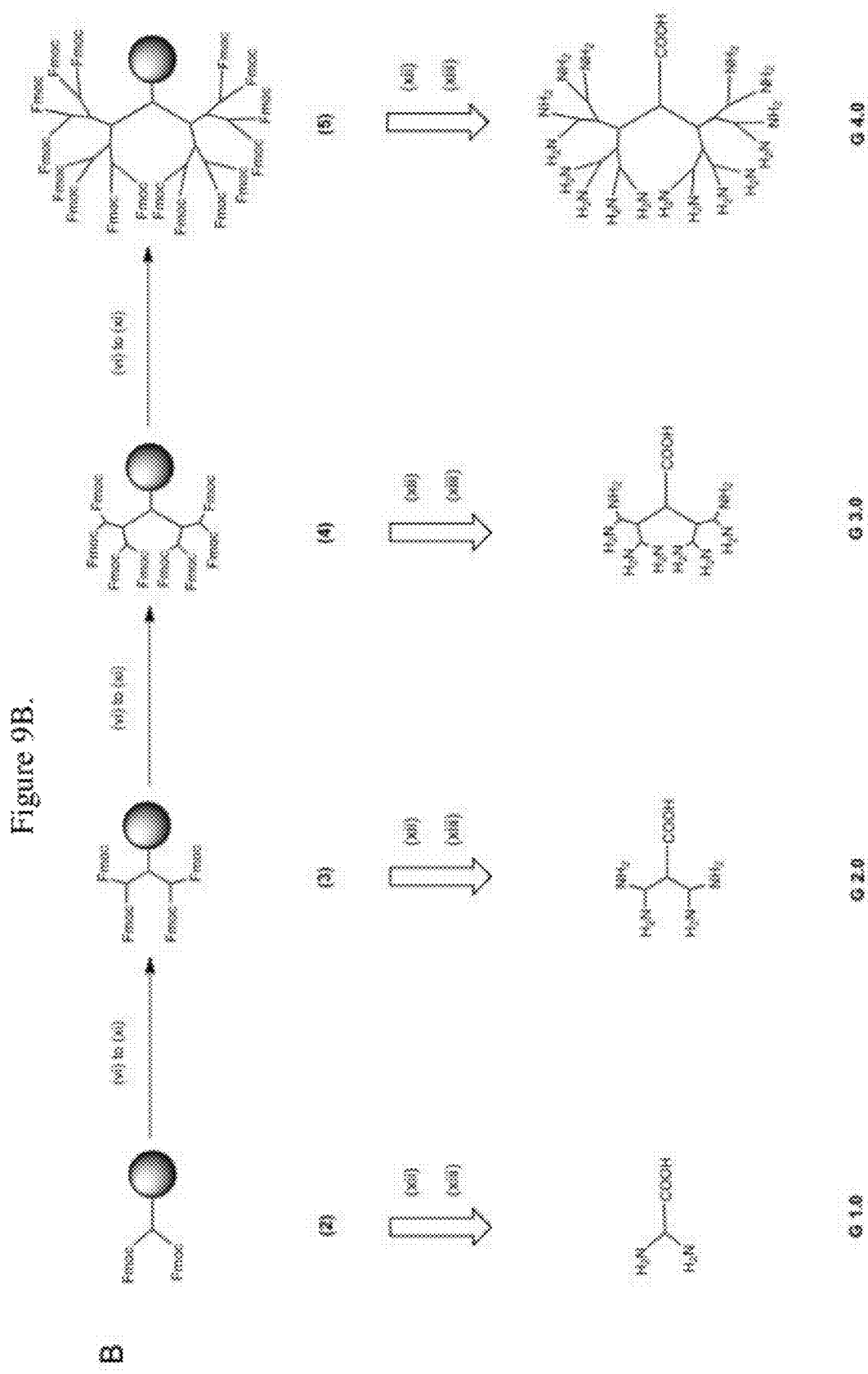
(FIG. 9B) G2.0-4.0.

The next generation dendrons were synthesized from resin-bound dendrons of previous generation using a procedure described above for the synthesis of G1.0 (FIG. 9B). For example, the dendrons G2.0 were obtained by sequentially coupling Fmoc-K(Fmoc)-OH, Fmoc-β-A-OH, and Fmoc-PEG$_6$-OH to resin-bound dendron G1.0 (2). Similarly, the PEGtide dendrons G3.0 and 4.0 were obtained from resin-bound dendrons G2.0 (3) and G3.0 (4), respectively. Thus, each PEGtide dendron contains monodisperse PEG (MW: 565.65 Da) interspersed with dipeptide lysine-alanine (-K-β-A-). The number of free terminal amino groups in G1.0, 2.0, 3.0, and 4.0 are 2, 4, 8, and 16, respectively that can be utilized for further modification with drugs, targeting groups, and imaging moieties.

All dendrons were purified by HPLC, and characterized using MALDI-TOF and DLS. The purity of PEGtide dendrons was determined using HPLC equipped with fluorescence detector. A fluorescence detector (Ex/Em: 492/518 nm) was employed because the first lysine incorporated in the dendron core was labeled with 5-FAM. The retention times of PEGtide dendron, G1.0-4.0, were found as 33.48, 35.05, 37.96, and 39.37 min, respectively. Thus, the retention time increased with increase in generation of dendrons because the avidity of binding to the column increases with contact area between the surfaces, as well as the binding strength of each interaction. Similar behavior has been reported for amine terminated PAMAM dendrons. The HPLC profiles also demonstrated that dendrons were obtained in high purity. The percentage purities of G1.0-4.0 dendrons were found as 98.3, 99.0, 96.8, and 98.9, respectively.

Figure 10:
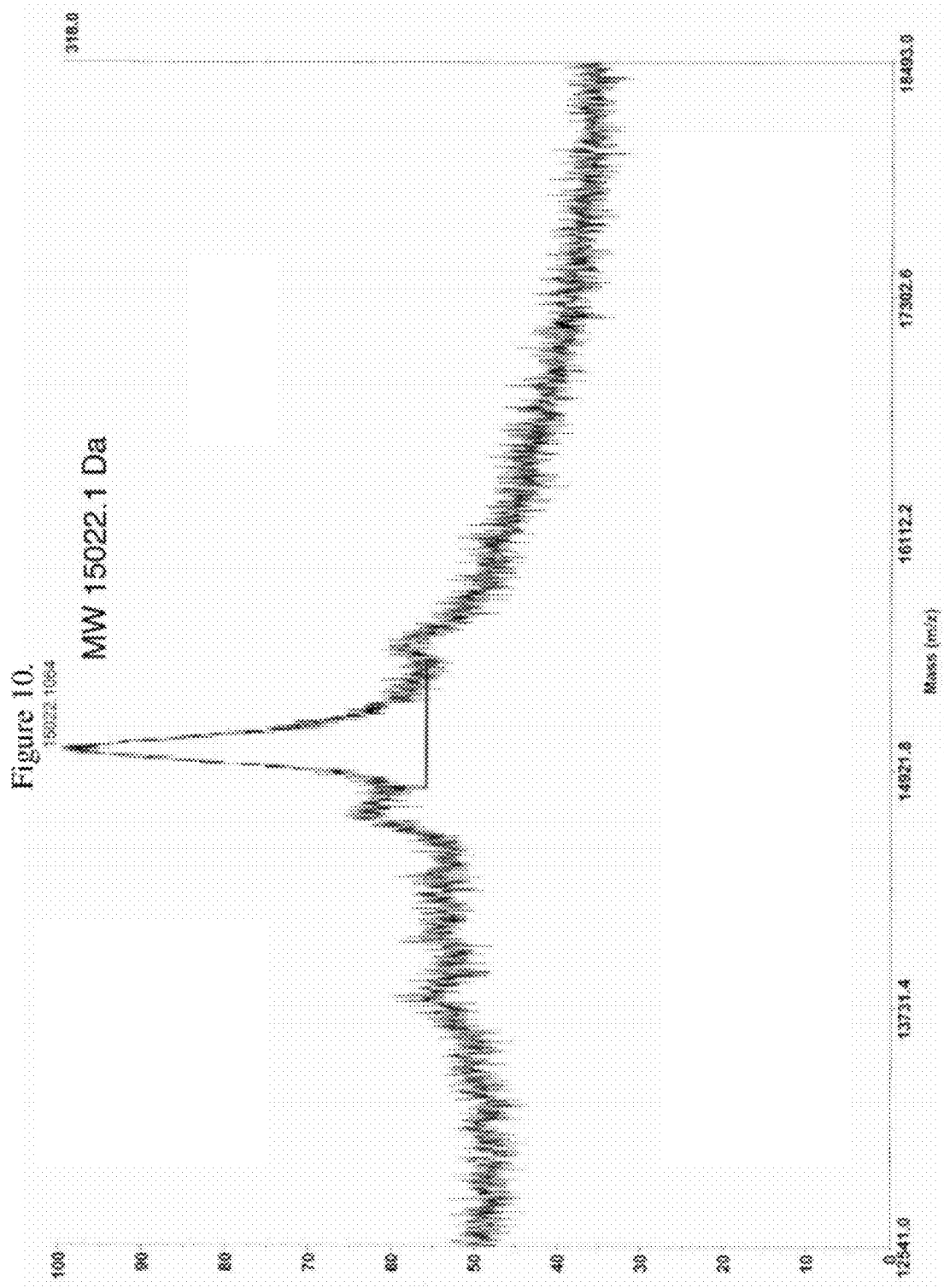
FIG. 10 is a MALDI-TOF spectrum of a generation 4.0 (G4.0) PEGtide dendron.

The molecular weights of PEGtide dendron G1.0-4.0 were determined using MALDI-TOF. The molecular weights of G1.0, G2.0, G3.0, and G4.0 were estimated as 1849.72, 3730.31, 7486.30, and 15022.1 Da, respectively, which were in agreement with calculated values of 1851.68, 3733.06, 7497.30, and 15023.77 Da. A representative MALDI-TOF spectrum of purified PEGtide dendron G4.0 is shown in FIG. 10. The signal intensity was relatively low when compared to spectra of low generation dendrons (G1.0-3.0). This is because larger molecule require more laser power for desorption and ionization process. Nevertheless, the ratio of signal to noise was still higher than 10. It must be mentioned that in each case single molecular weight peak was obtained, which is not characteristics of PEG polymers. This single molecular weight peak is due to the use of monodisperse PEG in dendron structure.

The hydrodynamic radii of PEGtide dendrons, G1.0-4.0, were determined using DLS. The radii for G1.0, G2.0, G3.0, and G4.0 dendrons were determined as 28.2, 65.4, 86.4, 114.3 nm. Thus, hydrodynamic radii increased with increase in generation of dendrons, which was not unexpected because hydrodynamic radii of peptides, proteins, and polymers are known to increase with increasing molecular weights. The narrow size distribution of dendrons points to the advantage of using mono-disperse PEG in dendron structure.

Example 1E

Synthesis of G3.0-Mannose

The purified PEGtide dendron G3.0 (7.5 mg, 1 µmole) and α-D-mannopyranosylphenyl isothiocyanate (10.0 mg, 32 µmole) were dissolved in a sodium carbonate buffer solution (0.1 M, pH 9.0, 5 mL) and stirred at room temperature for 12 hrs in dark. The crude product was purified by dialysis (MWCO 3,000 Da) in water for 24 hrs, and lyophilized. The purified product, PEGtide dendron with octavalent mannose cluster, was stored at −20° C. and further purified by HPLC. Yield: 8.3 mg (83%). MALDI-TOF: MW: calcd. 10003.9 Da. found 10009.9 Da.

Synthesis and Characterization of PEGtide dendron G3.0 Containing Octavalent Mannose Cluster (G3.0-Mannose)

Figure 12:
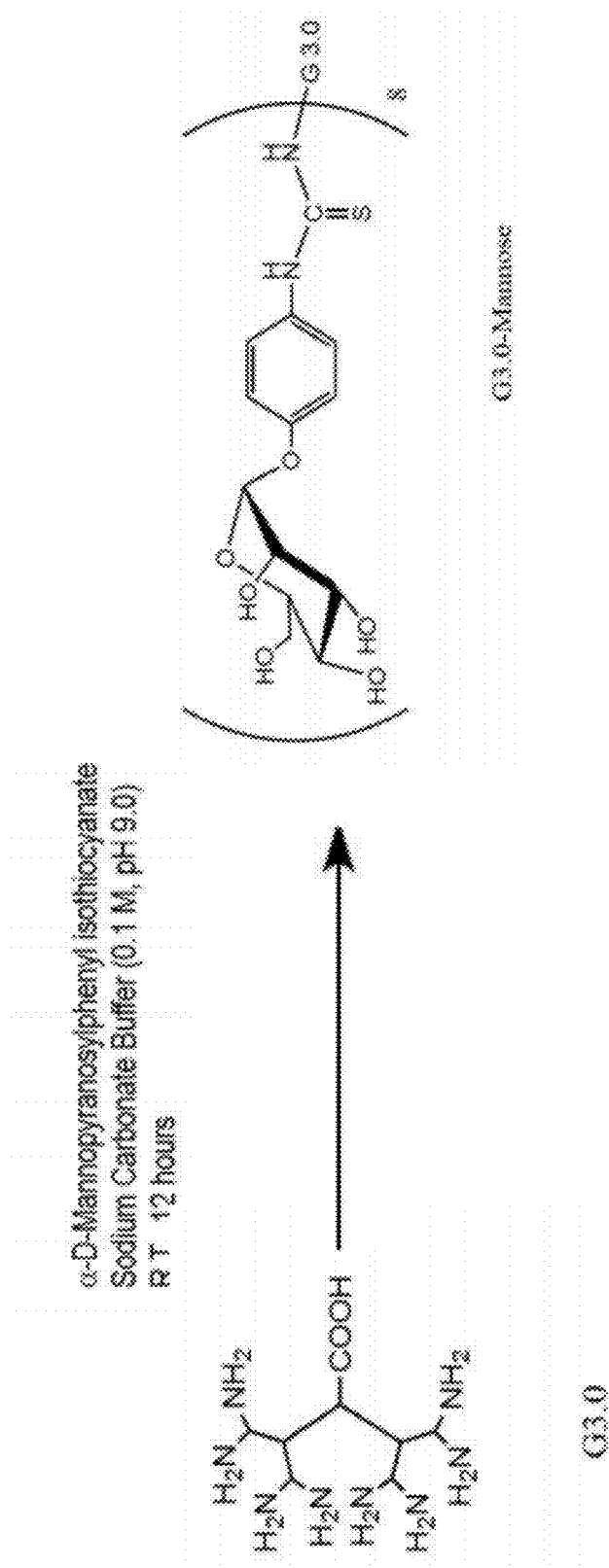
FIG. 12 is a schematic of the synthesis of PEGTide dendron G3.0 containing octavalent mannose cluster (G3.0-Mannose).
Figures 13, 14:
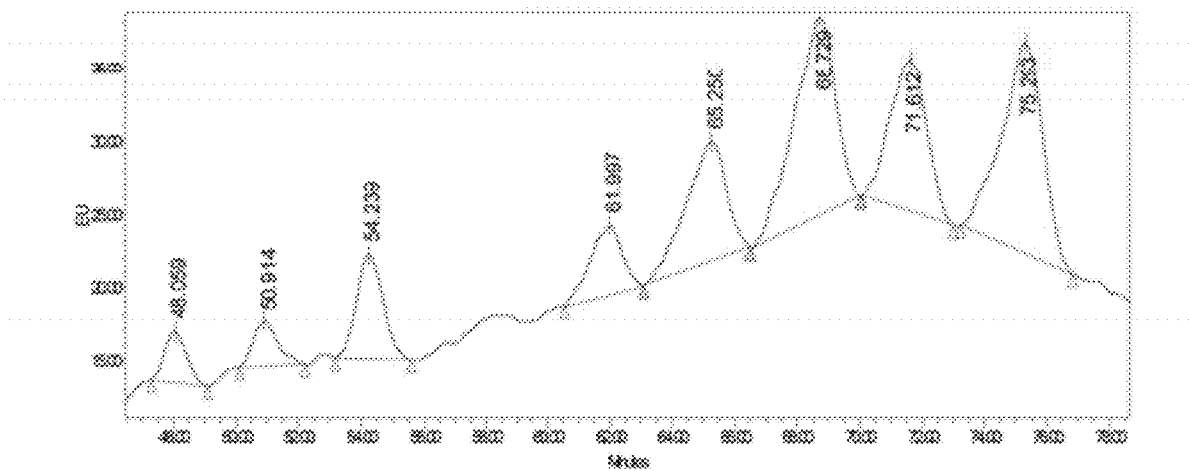
FIG. 13. is a HPLC profile of crude G3.0-Mannose.
FIG. 14 is a MALDI-TOF spectrum of purified G3.0-Mannose. The observed molecular weight is 10009.9 Da, whereas the calculated molecular weight is 10003.9 Da. The observed molecular weight corresponds to attachment of eight mannose moieties on dendron surface.
Figure 15:
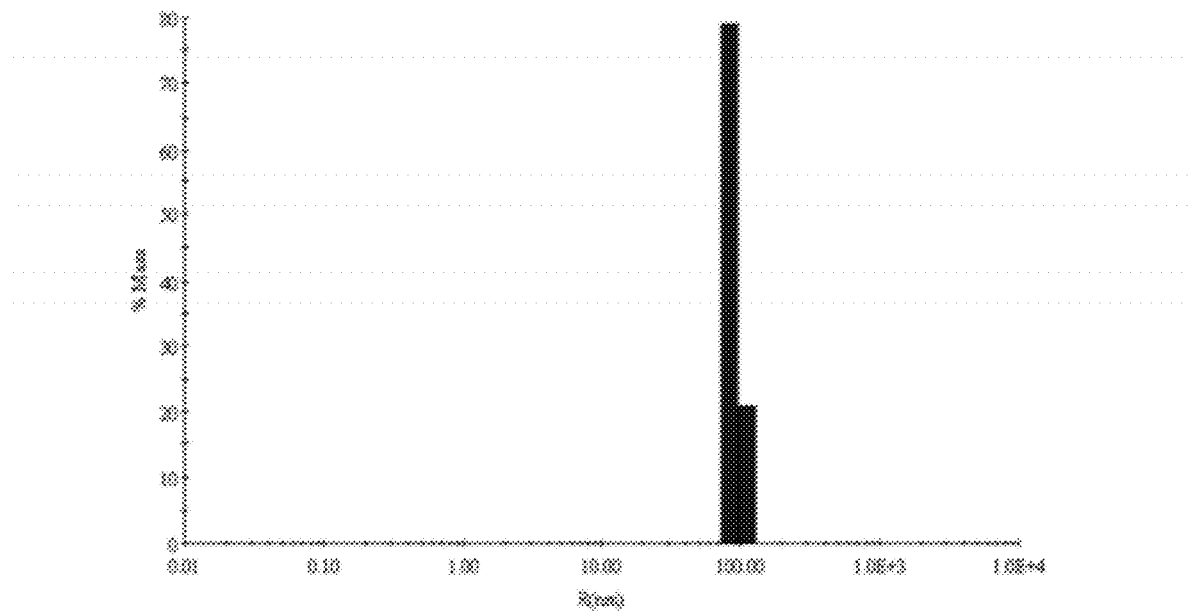
FIG. 15 shows the results of dynamic light scattering (DLS) analysis of purified G3.0-Mannose.

To obtain dendrons containing octavalent mannose cluster, α-D-mannopyranosylphenyl isothiocyanate was coupled to PEGtide G3.0 at room temperature in buffer (pH, 9.0) (as illustrated in FIG. 13). The coupling reaction used here involves the attack of nucleophile on the central electrophilic carbon of the isothiocynate group, leading to the formation of thiourea (FIG. 12). The G3.0-Mannose was purified by dialysis (MWCO: 3000 Da) in water. Despite the dialysis, the HPLC profile of the conjugate showed presence of several impurities, possibly due to the coupling of varying number of mannose moieties to G3.0 dendron. Therefore, G3.0-Mannose was further purified using HPLC, and fraction corresponding to retention time of 75.3 min was collected. The molecular weight of purified conjugate was estimated as 10009.9 Da using MALDI-TOF, which was in agreement with calculated value of 10003.9 Da, corresponding to attachment of eight mannose moieties onto the dendron (as illustrated in FIG. 14). The hydrodynamic radius of conjugates was estimated as 90.6 nm by DLS (as illustrated in FIG. 15), which was only slightly higher than PEGtide G3.0, with hydrodynamic radius of 86.4 nm.

Example 1F

Figure 8:
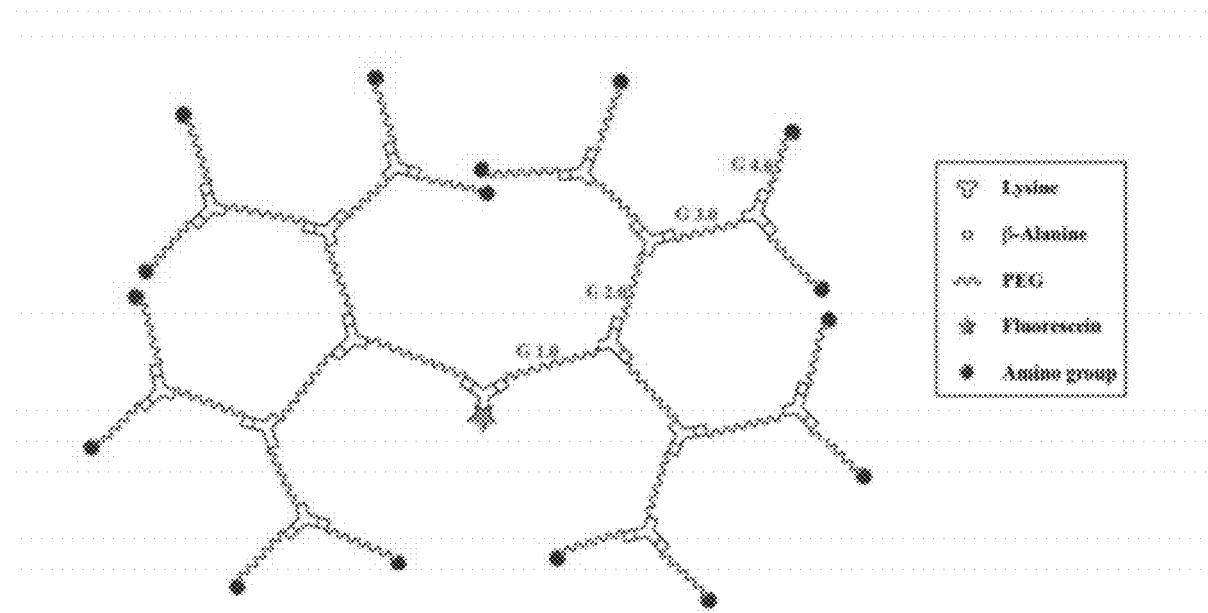
FIG. 8 depicts the structure of PEGTide dendron, G4.0, containing alternating monodisperse PEG polymer (MW: 575.65 Da) and dipeptide (lysine-β-alanine).

Synthesis and Characterization of PEGtide Dendron G4.0 (as Illustrated in FIG. 8)

(1) 100 mg of Fmoc-β-Ala-Wang Resin (0.36 mmole/g) was swelled in N,N-dimethylformamide (DMF) in PD-10 column for 10 minutes then drained.

(2) 4 mL of piperidine in DMF (1:4 of volume ratio) was added to resin for continually shaking 20 minutes then drained.

(3) The resin was washed by DMF solvent (4 mL×3) and monitored by Kaiser Test. Moved to next cycle if the small part of resin showed blue after Kaiser Test, otherwise repeated step (2).

(4) 7.3 mg of Fmoc-Lys(5-FAM)-OH (0.01 mmole), 5.4 mg of 1-Hydroxybenzotriazole hydrate (HOBT) (0.04 mmole), 20.8 mg of Benzotriazole-1-yl-oxy-tris-pyrrolidino-phosphonium hexafluorophosphate (PyBOP) and 13.2 µL N,N-diisopropylethylamine (DIEA) (0.08 mmole) were dissolved into 2 mL DMF solution, then transferred to PD-10 column and put on a shaker for continually shaking 4 hours.

(5) Wash the resin with DMF solvent (4 mL×3). 24.5 µL of Acetic anhydride (0.26 mmole) and 17.2 µL of DIEA (0.1 mmole) dissolved in 2 mL DMF solution was added to PD-10 column and shook for blocking free amino groups on resin.

(6) The resin was washed by DMF solvent (4 mL×3) and monitored by Kaiser Test. Moved to next cycle if the small part of resin showed transparent after Kaiser Test, otherwise repeated step (5).

(7) Repeat steps (2) and (3).

(8) 23.0 mg of Fmoc-PEG6-OH (0.04 mmole), 5.4 mg of HOBT (0.04 mmole), 20.8 mg of PyBOP (0.04 mmole) and 13.2 µL of DIEA (0.08 mmole) were dissolved in 2 mL of DMF, and then transferred to PD-10 column for continually shaking 4 hours.

(9) Repeat steps (6) and (7).

(10) 23.6 mg of Fmoc-Lys(Fmoc)-OH (0.04 mmole), 5.4 mg of HOBT (0.04 mmole), 20.8 mg of PyBOP (0.04 mmole) and 13.2 µL of DIEA (0.08 mmole) were dissolved in 2 mL of DMF, and then transferred to PD-10 column for continually shaking 4 hours.

(11) Repeat steps (6) and (7).

(12) 24.9 mg of Fmoc-β-Ala-OH (0.08 mmole), 10.8 mg of HOBT (0.08 mmole), 41.6 mg of PyBOP (0.08 mmole) and 26.4 µL of DIEA (0.16 mmole) were dissolved in 2 mL of DMF, and then transferred to PD-10 column for continually shaking 4 hours.

(13) Repeat steps (6) and (7).

(14) 46.1 mg of Fmoc-PEG6-OH (0.08 mmole), 10.8 mg of HOBT (0.08 mmole), 41.6 mg of PyBOP (0.08 mmole) and 26.4 µL of DIEA (0.16 mmole) were dissolved in 2 mL of DMF, and then transferred to PD-10 column for continually shaking 4 hours.

(15) Repeat steps (6) and (7).

(16) 47.3 mg of Fmoc-Lys(Fmoc)-OH (0.08 mmole), 10.8 mg of HOBT (0.08 mmole), 41.6 mg of PyBOP (0.08 mmole) and 26.4 µL of DIEA (0.16 mmole) were dissolved in 2 mL of DMF, and then transferred to PD-10 column for continually shaking 4 hours.

(17) Repeat steps (6) and (7).

(18) 49.8 mg of Fmoc-β-Ala-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(19) Repeat steps (6) and (7).

(20) 92.1 mg of Fmoc-PEG6-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(21) Repeat steps (6) and (7).

(22) 94.5 mg of Fmoc-Lys(Fmoc)-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(23) Repeat steps (6) and (7).

(24) 99.6 mg of Fmoc-β-Ala-OH (0.32 mmole), 43.2 mg of HOBT (0.32 mmole), 166.5 mg of PyBOP (0.32 mmole) and 105.8 µL of DIEA (0.64 mmole) were dissolved in 2 mL of DMF, and then transferred to PD-10 column for continually shaking 4 hours.

(25) Repeat steps (6) and (7).

(26) 184.2 mg of Fmoc-PEG6-OH (0.32 mmole), 43.2 mg of HOBT (0.32 mmole), 166.5 mg of PyBOP (0.32 mmole) and 105.8 µL of DIEA (0.64 mmole) were dissolved in 2 mL of DMF, and then transferred to PD-10 column for continually shaking 4 hours.

(27) Repeat steps (6) and (7).

(28) 189.0 mg of Fmoc-Lys(Fmoc)-OH (0.32 mmole), 43.2 mg of HOBT (0.32 mmole), 166.5 mg of PyBOP (0.32 mmole) and 105.8 µL of DIEA (0.64 mmole) were dissolved in 2 mL of DMF, and then transferred to PD-10 column for continually shaking 4 hours.

(29) Repeat steps (6) and (7).

(30) 199.2 mg of Fmoc-β-Ala-OH (0.64 mmole), 86.5 mg of HOBT (0.64 mmole), 333.0 mg of PyBOP (0.64 mmole) and 211.5 µL of DIEA (1.28 mmole) were dissolved in 2 mL of DMF, and then transferred to PD-10 column for continually shaking 4 hours.

(31) Repeat steps (6) and (7).

(32) 368.4 mg of Fmoc-PEG6-OH (0.64 mmole), 86.5 mg of HOBT (0.64 mmole), 333.0 mg of PyBOP (0.64 mmole) and 211.5 µL of DIEA (1.28 mmole) were dissolved in 2 mL of DMF, and then transferred to PD-10 column for continually shaking 4 hours.

(33) Repeat steps (6) and (7).

(34) Washed resin with Dichloromethane (DCM) and Methanol for three times each, and then dried the resin under vacuum overnight.

(35) Cleavage cocktail was prepared with Trifluoroacetic acid (TFA), Triisopropylsilane (TIS) and water (95:2.5:2.5 in volume ratio). The cocktail was added to resin for continually shaking 2 hours at room temperature.

(36) Collected the cleavage filtrate and evaporated the cleavage cocktail by rotavapor.

(37) Purified the crude product by semi-preparative HPLC and the organic solvent was removed by rotavapor.

(38) The purified PEGtide dendron G4.0 was obtained by lyophilizer.

Figure 11:
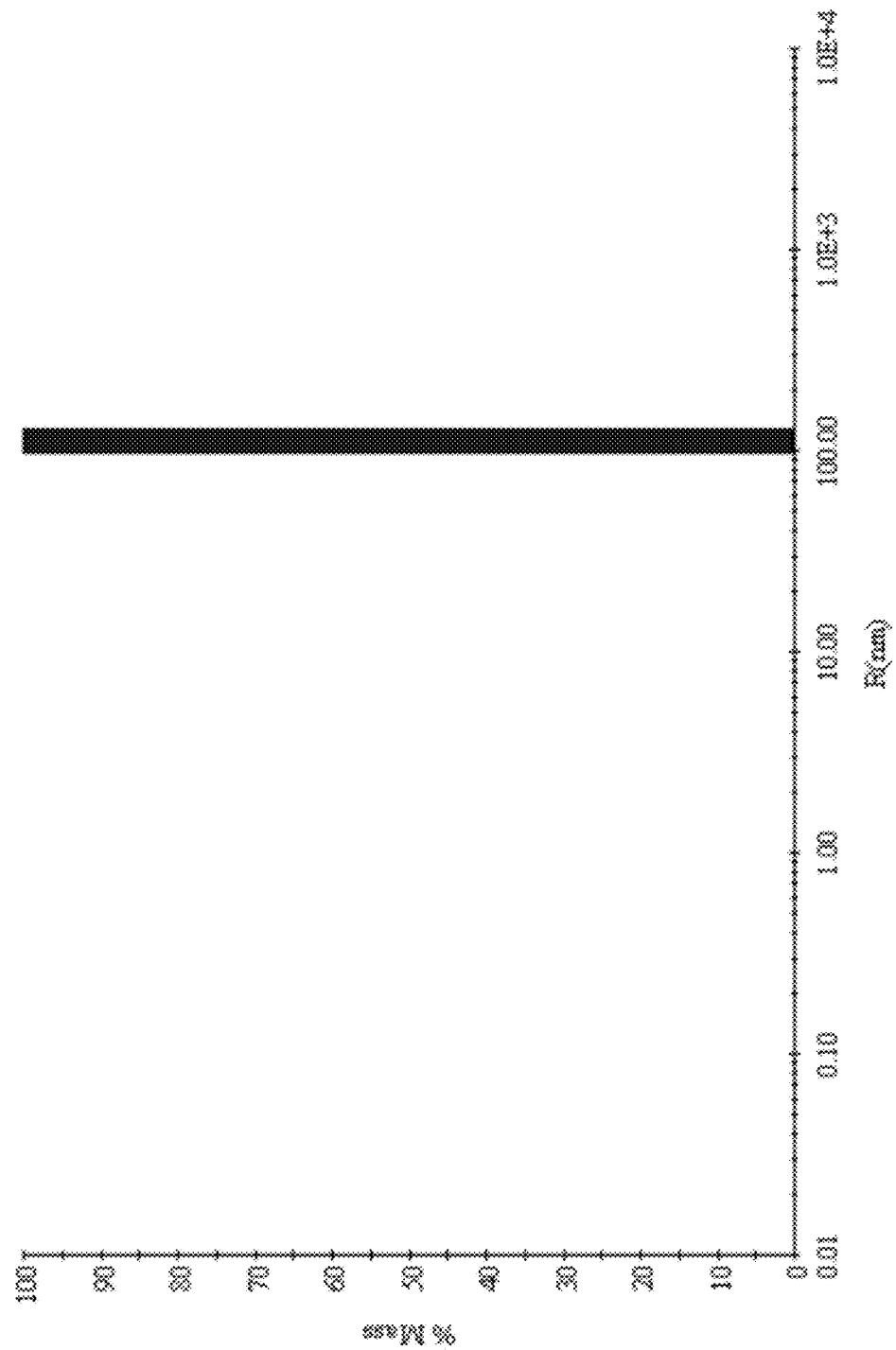
FIG. 11 shows the results of dynamic light scattering (DLS) analysis of a generation 4.0 (G4.0) PEGtide dendron, which shows that the dendron has a radius of 114.3 nm.

(39) Characterize PEGtide dendron G4.0 with Dynamic Light Scattering (DLS) and MALDI-TOF (as illustrated in FIG. 11).

Example 1G

Synthesis and Characterization of G2.0-DV3

(1) Synthesis PEGtide dendron G2.0 according to steps from (1) to (20) in EXAMPLE 1F.

(2) The resin was washed by DMF solvent (4 mL×3) and monitored by Kaiser Test. Moved to next step if the small part of resin showed transparent after Kaiser Test, otherwise repeated last one coupling step.

(3) 4 mL of piperidine in DMF (1:4 of volume ratio) was added to resin for continually shaking 20 minutes then drained.

(4) The resin was washed by DMF solvent (4 mL×3) and monitored by Kaiser Test. Moved to next cycle if the small part of resin showed blue after Kaiser Test, otherwise repeated step (3).

(5) 47.6 mg of Fmoc-Gly-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(6) Repeat steps (2) to (4).

(7) 75.0 mg of Fmoc-Lys(Boc)-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(8) Repeat steps (2) to (4).

(9) 65.8 mg of Fmoc-Asp(OtBu)-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(10) Repeat steps (2) to (4).

(11) 54.0 mg of Fmoc-Pro-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(12) Repeat steps (2) to (4).

(13) 103.8 mg of Fmoc-Arg(Pbf)-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(14) Repeat steps (2) to (4).

(15) 99.2 mg of Fmoc-His(Trt)-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(16) Repeat steps (2) to (4).

(17) 84.3 mg of Fmoc-Trp(Boc)-OH (0.16 mmole), 21.6 mg of HOBT (0.16 mmole), 83.2 mg of PyBOP (0.16 mmole) and 52.9 µL of DIEA (0.32 mmole) were dissolved in 2 mL of DMF, and then transferred to PD-10 column for continually shaking 4 hours.

(18) Repeat steps (2) to (4).

(19) 61.3 mg of Fmoc-Ser(tBu)-OH (0.16 mmole), 21.6 mg of HOBT (0.16 mmole), 83.2 mg of PyBOP (0.16 mmole) and 52.9 μL of DIEA (0.32 mmole) were dissolved in 2 mL of DMF, and then transferred to PD-10 column for continually shaking 4 hours.

(20) Repeat steps (2) to (4).

(21) 49:8 mg of Fmoc-Ala-OH (0.16 mmole), 21.6 mg of HOBT (0.16 mmole), 83.2 mg of PyBOP (0.16 mmole) and 52.9 μL of DIEA (0.32 mmole) were dissolved in 2 mL of DMF, and then transferred to PD-10 column for continually shaking 4 hours.

(22) Repeat steps (2) to (4).

Using MALDI-TOF, purified DV3-G2.0 collected from semi-preparative HPLC purification, the calculated and found molecular weights are 8554.5 Da and 8547.6 Da, respectively.

Example 2

Macrophage Uptake of Dendrons

J774.E murine macrophage cells were grown as attached cells in a $CO_2$ water-jacketed incubator (Form a Scientific Inc., Marietta, Ohio) with a humidified 5% $CO_2$ atmosphere at 37° C. The cells were maintained in RPMI-1640 (GIBCO) containing 10% fetal bovine serum (FBS), 100 U/mL penicillin, and 100 μg/mL streptomycin/mL. The cells were seeded two days before experiment to 24-well plates at $0.5 \times 10^5$ cells/well for quantitative uptake measurement or to chambered coverglass (LAB-TEK II) at $1 \times 10^5$ cell/chamber for confocal microscopy. Cells were incubated with G3.0-Mannose (40 nM) in HBSS at 37° C. for 1 hr. For confocal microscopy, the incubation included the additional 0.16 mg/mL of the general endocytosis marker rhodamine B-labeled dextran (10,000 MW) and the nuclear dye DAPI. For Mannan inhibition studies, cells were pre-incubated with mannan (10 mg/mL) for 1 hr, followed by incubation with G3.0-Mannose, with or without rhodamine B-dextran/DAPI plus 10 mg/mL of mannan. After incubation, the unbound molecules were washed thrice using cold DPBS buffer. PEGtide dendron G3.0 (40 nM) (without mannose) was used as a negative control of mannose receptor-mediated cellular uptake.

The buffer was collected after 1 hr incubation and filtered through a Microcon (NMWL: 3 kDa) to demonstrate that no detectable free fluorescence had been produced during the 1 hr incubation time. In quantitative uptake experiments, the washed cells were lysed in wells overnight with 150 μL of 1 N NaOH solution and neutralized the next day with 150 μL of 1 N HCl solution, resulting in 300 μL of cell lysate/well. 250 μL of cell lysate was transferred to a well of a 96-well plate for 5-FAM fluorescence measurement on Tecan GENIOS fluorescent plate reader (Phenix Research Products, Hayward, Calif.). The total cell-associated fluorescence reading was converted into total cell-associated dendron amount using a separately established dendron's fluorescence standard curve. A small fraction of the lysate (about 50 μL, depending on cell density plated) was used to determine total cellular protein/well by Bradford Protein Assay. The total cellular protein/well was used to normalize the dendron amount/well to correct well-to-well variation in cell mass. To demonstrate that the total cell-associated dendron amount was mostly due to internalized fluorescence, as opposed to cell-surface-bound fluorescence, confocal microscopy was carried out in a Z-stack scanning mode on a Leica TCS SP5 confocal microscope (Leica Microsystems Inc., Buffalo Grove, Ill.).

Figure 16:
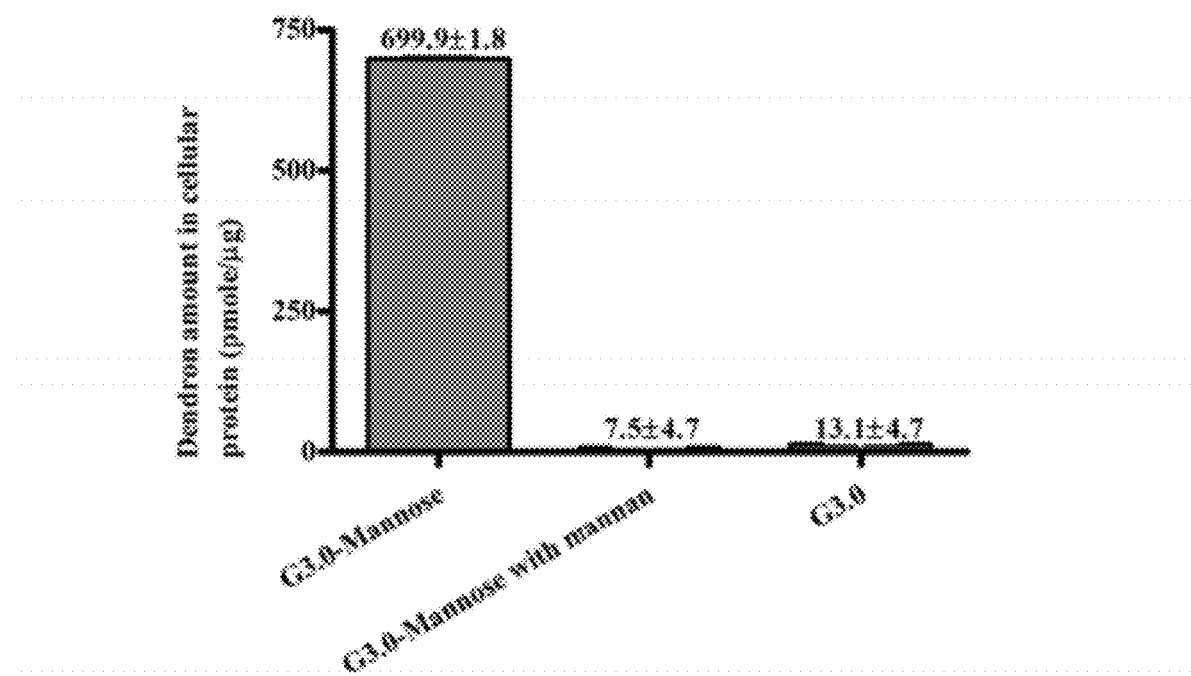
FIG. 16. represents uptake and mannan inhibition of G3.0 Mannose in J774.e murine macrophage cells.

The quantitative uptake of G3.0-Mannose in macrophage was 699.6±1.8 pmole/μg, whereas that of non-mannosylated G3.0 (control) was 13.1±4.7 pmole/μg, indicating a 53-fold specificity for mannose receptor. The mannose analog mannan inhibited the G3.0-Mannose uptake to 7.5±4.7 pmole/μg, further suggesting that the uptake was mannose receptor-mediated (FIG. 16).

To demonstrate that the uptake of total cellular dendron amount is mostly intracellular, the confocal microscopy was carried out. Punctuate red fluorescence of the fluid endocytosis marker rhodamine B-labeled dextran was significant in both treatments, indicating that the general fluid endocytosis was normal in both experimental settings, regardless of the expected engagement of mannose receptor by G3.0-Mannose.

In contrast, the intracellular green fluorescence from 5-FAM conjugated G3.0-Mannose was prominent only in G3.0-Mannose treated cells but not in G3.0 treated cells, suggesting that G3.0-Mannose was taken into cells in a mannose receptor-dependent manner. Since little cell surface green fluorescence was present, the images suggested little cell surface binding and the total cellular associated G3.0-Mannose reflected mostly internalized G3.0-Mannose dendrons. The punctuate appearance of the green fluorescence and its co-localization with the red fluid endocytosis marker suggested that G3.0-Mannose was internalized through endosytosis. As expected, all punctuate green fluorescence merged with punctuate red fluorescence but not vice versa, suggesting that mannose receptor-mediated G3.0-Mannose endocytosis uses only one of the several occurring endocytosis pathways.

Example 3

Cell Viability—MTT Assay of PEGtide Dendron G3.0 and G3.0-Mannose

Method (1) Prepared MTT solution in PBS (pH 7.4) with final concentration of 5 mg/mL.

(2) Cultured J774.E muring macrophage cells with G3.0-Mannose, G3.0 and PAMAM G1.0, with each concentration of 40 nM, in HBSS for 2 hours. 6 replicates were applied. (n=6).

(3) Aspirated off the culture medium and washed with DPBS for three times for each well.

(4) 100 μL of HBSS and 25 μL of MIT solution were added to each well. Placed the plate in incubator at 37° C. overnight.

(5) Aspirated off the HBSS/MTT solution. Added 200 μL of DMSO for dissolving the crystals.

(6) Transferred to plate reader and measure the absorption at 570 nm.

Results (6) Transferred to plate reader and measure the absorption at 570 nm.

Figure 17:
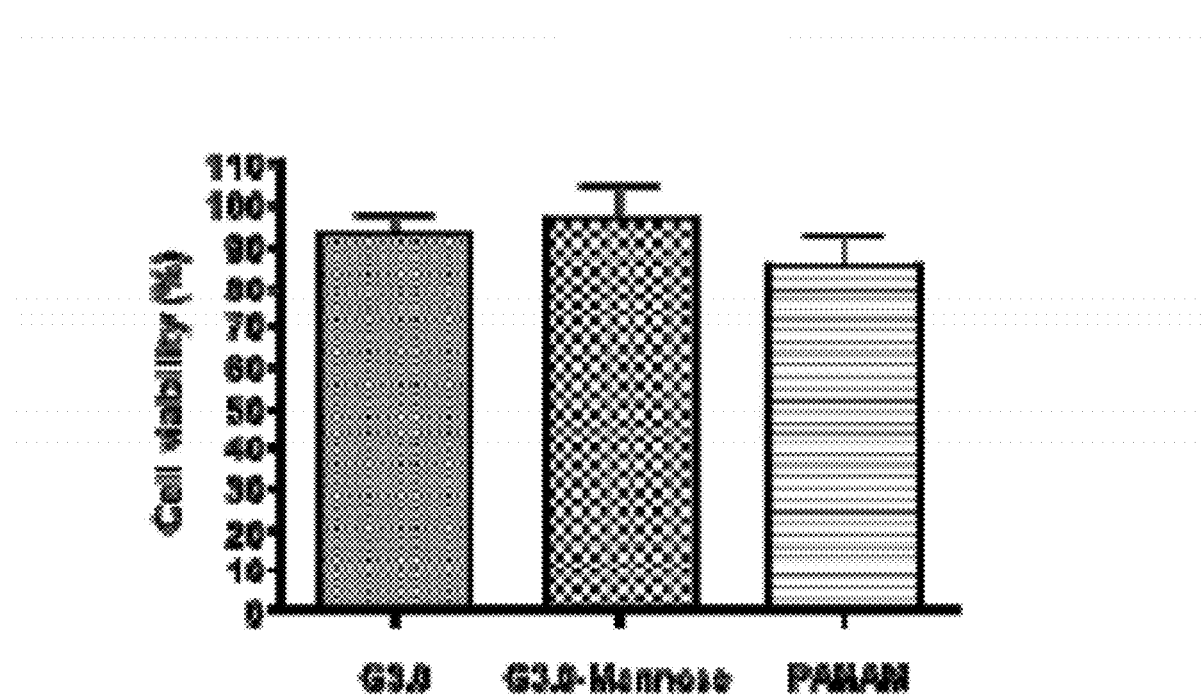
FIG. 17 represents the MMT assay of PEGtide Dendron G3.0 and G3.0-Mannose in J74.E murine macrophage cells, PAMAM dendrimer G1.0 was used as a negative control.

The cell relative viabilities of G3.0, G3.0-Mannose and PAMAM (G1.0) were 92.96±4.44%, 96.40±7.81% and 85.45±7.06%, respectively. Values represent mean±standard deviation (n=6), see FIG. 17.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, and patent applications cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A carrier for in vivo delivery of a therapeutic agent according to Formula I:

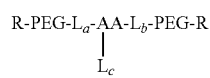
(I)

wherein R is:

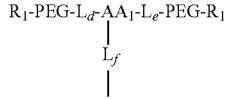

$R_1$ is:

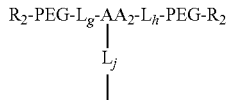

$R_2$ is:

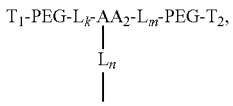

wherein PEG is linear or branched poly(ethylene glycol); AA, $AA_1$, $AA_2$, and $AA_3$ are each independently lysine or ornithine;

$L_a$, $L_b$, $L_c$, $L_d$, $L_e$, $L_f$, $L_g$, $L_h$, $L_j$, and $L_n$ are each independently 0-1 amino acids long and selected from the group consisting of alanine, cysteine, arginine, 4-aminobutyric acid, 6-aminohexanoic acid and α-amino-butyric acid;

$L_k$ and $L_m$ are each independently 0-1 amino acids long and selected from the group consisting of alanine, glycine, valine, leucine, isoleucine, phenylglycine, phenylalanine, cysteine, arginine, histidine, norvaline, norleucine, 2-fluorophenylalanine, 3-fluorophenylalanine, 4-fluorophenylalanine, and β-cyclohexyl-alanine; and $T_1$ and $T_2$ are each a final PEG terminus independently selected from the group consisting of an amino group, acetyl group, fluorenylmethyloxycarbonyl group, therapeutic agents, diagnostic agents, biologic agents, targeting agents and adjuvants.

2. The composition of claim 1, wherein $L_c$ is selected from the group consisting of cysteine and alanine.

3. The composition of claim 1, wherein Formula (I) is:

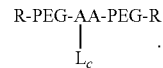

4. The composition of claim 1, wherein R is:

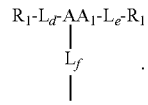

5. The composition of claim 1, wherein $R_1$ is:

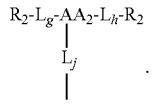

6. The composition of claim 1, wherein $R_2$ is:

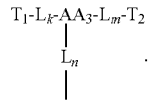

7. The composition of claim 1, wherein $R_2$ is:

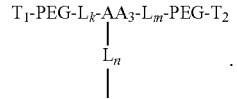

8. The composition of claim 1, wherein $R_2$ is $T_1$ or $T_2$.

9. The composition of claim 1, wherein $L_a$, $L_b$, $L_c$, $L_d$, $L_f$, $L_g$, $L_h$, $L_j$, $L_k$, $L_m$ and $L_n$ are selected from the group consisting of alanine, and arginine; and $T_1$ and $T_2$ are fluorenylmethyloxycarbonyl protected amino groups.

10. The composition of claim 9, wherein $L_a$, $L_b$, $L_c$, $L_d$, $L_e$, $L_f$, $L_g$, $L_h$, $L_j$, $L_k$, $L_m$ and $L_n$ are each alanine.

11. A pharmaceutical composition comprising the composition of claim 1 and at least one loaded therapeutic agent.

12. A pharmaceutical composition comprising the composition of claim 1 wherein the therapeutic agent is a pharmaceutical active, diagnostic agent, biologic agent, imaging agent, targeting agent or an adjuvant.

13. A composition comprising the composition of claim 1, a therapeutic agent and a pharmaceutically acceptable carrier.

14. The composition of claim 13, wherein the therapeutic agent is an antineoplastic therapeutic agent.

15. The composition of claim 13, wherein the therapeutic agent is an antiretroviral therapeutic agent.

16. The pharmaceutical composition of claim 13, wherein said therapeutic agent is an antigen capable of stimulating an immune response.

* * * * *